(12) United States Patent
Lu

(10) Patent No.: US 7,939,016 B2
(45) Date of Patent: May 10, 2011

(54) ARTICLE PROCESSING APPARATUS AND RELATED METHOD

(75) Inventor: Michael Lu, Lexington, MA (US)

(73) Assignee: BioDefense Corporation, Boston, MA (US)

( * ) Notice: Subject to any disclaimer, the term of this patent is extended or adjusted under 35 U.S.C. 154(b) by 0 days.

(21) Appl. No.: 12/692,284

(22) Filed: Jan. 22, 2010

(65) Prior Publication Data

US 2010/0183476 A1 Jul. 22, 2010

Related U.S. Application Data

(60) Division of application No. 11/281,921, filed on Nov. 18, 2005, now Pat. No. 7,687,045, which is a continuation-in-part of application No. 11/050,651, filed on Feb. 4, 2005, now Pat. No. 7,507,369, which is a continuation-in-part of application No. 10/306,774, filed on Nov. 26, 2002, now abandoned.

(60) Provisional application No. 60/333,443, filed on Nov. 26, 2001.

(51) Int. Cl.
*A61L 2/00* (2006.01)
*B08B 3/12* (2006.01)
*B08B 6/00* (2006.01)
*B08B 7/00* (2006.01)
*B08B 7/02* (2006.01)

(52) U.S. Cl. ................ 422/22; 422/1; 422/24; 422/292; 422/300; 134/1

(58) Field of Classification Search .................... 422/22, 422/1, 24, 292, 300; 134/1
See application file for complete search history.

(56) References Cited

U.S. PATENT DOCUMENTS

| 4,109,397 | A | | 8/1978 | Daily |
| 4,896,010 | A | | 1/1990 | O'Connor et al. |
| 5,106,594 | A | | 4/1992 | Held et al. |
| 5,114,670 | A | | 5/1992 | Duffey |
| 5,173,257 | A | | 12/1992 | Pearson |
| 5,213,758 | A | | 5/1993 | Kawashima et al. |
| 5,213,759 | A | | 5/1993 | Castberg et al. |
| 5,238,660 | A | | 8/1993 | Dietwart |
| 5,546,678 | A | * | 8/1996 | Dhaemers ........................ 34/275 |
| 5,641,423 | A | | 6/1997 | Bridges et al. |
| 5,744,094 | A | | 4/1998 | Castberg et al. |

(Continued)

FOREIGN PATENT DOCUMENTS

DE 3505571 A1 8/1986

(Continued)

OTHER PUBLICATIONS

"$1 billion grant program to expand eventually to all 50 states", *Anthrax and Bioterror*, Jun. 7, 2002, http://www.msnbc.com/news/763649.asp, 3 pages.

(Continued)

*Primary Examiner* — Sean Conley
*Assistant Examiner* — Regina Yoo
(74) *Attorney, Agent, or Firm* — Finnegan, Henderson, Farabow, Garrett & Dunner LLP

(57) ABSTRACT

The present invention relates generally to systems and methods of disinfecting and/or decontaminating articles, and more specifically to a system and method of efficiently disinfecting and/or decontaminating articles such as pieces of mail that may have been exposed to diverse biological and/or chemical contaminants.

7 Claims, 12 Drawing Sheets

U.S. PATENT DOCUMENTS

| | | | |
|---|---|---|---|
| 5,788,940 A | | 8/1998 | Cicha et al. |
| 6,006,387 A * | | 12/1999 | Cooper et al. .................... 8/158 |
| 6,077,478 A | | 6/2000 | Sauer et al. |
| 6,375,697 B2 | | 4/2002 | Davies |
| 6,454,996 B1 | | 9/2002 | Lin et al. |
| 6,558,620 B1 | | 5/2003 | Sanford et al. |
| 6,749,806 B2 | | 6/2004 | Koji et al. |
| 2002/0168287 A1 | | 11/2002 | Eckhardt et al. |
| 2003/0085266 A1 | | 5/2003 | Simon |
| 2003/0086821 A1 | | 5/2003 | Matthew |
| 2003/0132398 A1 | | 7/2003 | Wang |
| 2004/0010476 A1 | | 1/2004 | Rumph et al. |
| 2004/0022665 A1 | | 2/2004 | Lu |
| 2004/0022668 A1 | | 2/2004 | Kitchen |
| 2004/0022670 A1 | | 2/2004 | Megerle et al. |
| 2004/0022671 A1 | | 2/2004 | Malatesta |
| 2004/0024278 A1 | | 2/2004 | Megerle |
| 2004/0259188 A1 | | 12/2004 | Rosenblatt et al. |
| 2005/0031485 A1 | | 2/2005 | Wen |
| 2005/0080373 A1 | | 4/2005 | Wang |
| 2005/0280536 A1 * | | 12/2005 | Hamilton et al. .......... 340/572.1 |

FOREIGN PATENT DOCUMENTS

| | | | |
|---|---|---|---|
| DE | 10008512 A1 | | 9/2001 |
| EP | 0320193 A2 | | 6/1989 |
| JP | 60165996 A | * | 8/1985 |
| JP | 60-205846 | | 3/1987 |
| JP | 6264998 A | | 3/1987 |
| WO | WO 94/20150 A1 | | 9/1994 |
| WO | WO 9961075 A1 | | 12/1999 |
| WO | WO 02/076513 A1 | | 10/2002 |
| WO | WO 03/039608 A2 | | 5/2003 |
| WO | WO 2004/032978 A2 | | 4/2004 |
| WO | WO 2006/083967 | | 8/2006 |

OTHER PUBLICATIONS

"Scientists propose developing new type of detector", Aug. 12, 2002, http://www.msnbc.com/news/793245.asp, 3 pages.

"Survival Equipment", http://www.survivalequipment.net/, 3 pages.

"What is Your Process for Handling Suspicious Mail?", http://www.safesorter.com, 1 page.

Alexeter BioDefense-Anthrax Test, http://www.alexeter.com/, Apr. 30, 2002, 5 pages.

Ananova, "Postal service's anti-anthrax machine may disrupt mail", Oct. 26, 2001, 1 page, http://www.ananova.com/news/storv/sm_434204.html?menu=news.technology, 1 page.

Bacou-Dalloz Company, Survivair, "Survivair® Model 1688 CN/CS/P100 Canister User Instructions", Aug. 2001, www.bacou-dalloz.com, 4 pages.

Centrex Inc. Press Release, "Centrex Appoints First Montauk Securities Corp.", Nov. 15, 2002, http://www.centrexcorporation.com/Press/111502A.htm, 2 pages.

Chemin du Cyclotron, Press Release, "IBA confirms that its advanced sterilization technologies can kill Anthrax spores", Oct. 23, 2001, Louvain-la-Neuve, Belgium, 2 pages.

Clean Air & Water Systems, Inc., "Ozone Air Clean—How Ozone Air Clean Works", http://www.ozonecaws.com/ozoneairclean.htm, 1 page.

European Search Report dated Oct. 2, 2009, from EP Application No. 09169605.4-2113.

Gilligan, Eliza, Electron Beam Irradiation, Feb. 15, 2002, http://palimpsest.stanford.edu/byform/mailing-lists/cdl/2002/0231.html, 4 pages.

Hulse, Carl, "Irradiating Mail to Congress May be Making Workers Ill", New York Times, published Jul. 2, 2002, 2 pages.

International Search Report for PCT/US2006/044246 dated Aug. 16, 2007.

Notice of Allowance dated Oct. 19, 2009 from U.S. Appl. No. 11/281,921.

Office Action dated Oct. 4, 2005 U.S. Appl. No. 10/306,774.

Office Action dated Dec. 4, 2008 from U.S. Appl. No. 10/306,774.

Office Action dated Dec. 13, 2007 from U.S. Appl. No. 11/050,651.

Office Action dated Feb. 22, 2007 from U.S. Appl. No. 10/306,774.

Office Action dated Feb. 22, 2008 from U.S. Appl. No. 10/306,774.

Office Action dated Jun. 27, 2008 from U.S. Appl. No. 11/050,651.

Office Action dated Mar. 18, 2009 from U.S. Appl. No. 11/281,921.

Office Action dated Jun. 11, 2009 from U.S. Appl. No. 10/306,774.

Office Action dated Jun. 27, 2008 U.S. Appl. No. 11/050,651.

Office Action dated Jul. 3, 2006 from U.S. Appl. No. 10/306,774.

Online NewsHour: Sterilizing the Mail, Dec. 3, 2001, http://www.pbs.org/newshour/bb/terrorism/july-dec01/sterilize_12-3.html, 2001.

PCT/US/2006/003568, International Search Report dated Jul. 3, 2006.

Pope Justin, "Companies Probe Use of Steam on Germs", Oct. 19, 2001, 2 pages, http://www.consteril.com/www/about_us/archive/companies_probe_steam_on_germs.htm, 2 pages.

U.S. Appl. No. 60/344,848 to Swider (provisional of U.S. App. Pub. No. 2004/0024278 to Mergerle), filed Dec. 31, 2001.

Rudakov, Dr. Leonid I., Berkeley Scholars, Inc., "Transportable, High-Power, Repetitive Electron-Beam Generator for Emergency Radiation Sterilization Applications", 2 pages.

Surebeam Corporation, "[cdn-nucl-II] SureBeam mail sterilization", Nov. 2, 2001, www.surebeam.com, 2 pages.

TD Waterhouse Research, "IGEN Accelerates Delivery of Tests to Department of Defense to Meet Increased Demand", Oct. 10, 2002, https://research.tdwaterhouse.com/waterhou.../news/asp?docKey=100-283p8315-1&Source=PR, 2 pages.

Testing Protocol for Safesorter, http://www.safesorter.com/testedandproven.htm Apr. 7, 2002, 2 pages.

Titan Scan Technologies, "Components of a MailSafe™ System" http://www.titanscan.com/mailsafe/systems.html, 1 page.

Titan Scan Technologies, "Mail Sanitization Systems", http://www.titanscan.com/mailsafe/index.html, 1 page.

Titan Scan Technologies, The Process—How MailSafe™ Works, http://www.titanscan.com/mailsafe/process.html, 1 page.

Titan Scan Technologies, Components of a MailSafe™ System, http://www.titanscan.com/mailsafe/systems.html, 1 page.

PCT Written Opinion for International Patent Application No. PCT/US2006/044246, dated Aug. 16, 2007.

\* cited by examiner

ARTICLE PROCESSING APPARATUS AND RELATED METHOD

CROSS REFERENCE TO RELATED APPLICATIONS

This application is a divisional application of U.S. patent application Ser. No. 11/281,921, filed Nov. 18, 2005, now U.S. Pat. No. 7,687,045 which is a continuation-in-part of U.S. patent application Ser. No. 11/050,651, now issued U.S. Pat. No. 7,507,369, filed Feb. 4, 2005, entitled ARTICLE PROCESSING APPARATUS AND RELATED METHODS, which is a continuation-in-part of U.S. patent application Ser. No. 10/306,774, now abandoned, filed Nov. 26, 2002, entitled MAIL BOX PROCESSOR, and claims the benefit of priority of U.S. Provisional Patent Application No. 60/333,443, filed Nov. 26, 2001, entitled MAIL BOX PROCESSOR, the entirety of all of which are incorporated herein by reference.

DESCRIPTION OF THE INVENTION

1. Field of the Invention

The present invention relates generally to systems and methods of disinfecting and/or decontaminating articles, and more specifically to a system and method of efficiently disinfecting and/or decontaminating articles such as pieces of mail that may have been exposed to diverse biological and/or chemical contaminants.

2. Background of the Invention

In recent years, there has been an increasing need for improved techniques of disinfecting and/or decontaminating articles that may have been intentionally or accidentally exposed to biological and/or chemical contaminants harmful to humans or animals. For example, such articles may have been inadvertently tainted with biological and/or chemical contaminants as a result of a laboratory or industrial accident. Alternatively, such articles may have been intentionally contaminated with harmful substances during the commission of a criminal or terrorist act.

Specifically, there is an increasing need for improved techniques of disinfecting and/or decontaminating articles that are shipped through the mail. This is because contaminated pieces of mail not only have the potential of harming the intended recipients of the mail and possibly those in the proximity of the intended recipients, but they can also harm significant numbers of other individuals such as postal employees who handle the contaminated mail as it passes through the postal system.

For example, the U.S. Postal Service has recently confronted the problem of handling letters that were contaminated with anthrax. Not only were recipients of the contaminated mail exposed to harmful anthrax spores, but numerous postal employees were also exposed to the anthrax spores leaking from the tainted letters, resulting in sickness, and in some cases, death. Further, significant numbers of people at the point of delivery of the contaminated letters were exposed to the anthrax. Because the anthrax spores released from the letters were transmitted through the air, entire buildings were contaminated by the spores via the buildings' heating and ventilation systems, resulting in the buildings' occupants being treated with powerful antibiotics to ward off anthrax-related illnesses. Moreover, because the anthrax-tainted letters contaminated some mail handling equipment at U.S. Post Offices, other mail passing through the postal system was tainted with the anthrax by cross-contamination, resulting in additional illness and deaths. Beyond the human toll, buildings and mail handling equipment were subjected to very costly decontamination procedures to remove the potentially harmful anthrax spores.

One way of guarding against contaminated articles from being shipped through the mail is to inspect each and every piece of mail at the point of entry into the postal system. However, this approach is generally regarded as unworkable because the U.S. Postal Service is estimated to handle hundreds of millions of pieces of mail each day. Further, the U.S. Postal Service currently has fewer than 2,000 postal inspectors charged with the task of investigating the misuse of the mail. Clearly, inspecting each piece of mail that passes through the postal system with such limited resources is virtually an insurmountable task.

Another approach to disinfecting and/or decontaminating pieces of mail is to irradiate the mail using electron beam technology. For example, bulk quantities of the mail may be irradiated by beams of high-energy electrons generated by an electron gun. Such technology has been employed to kill bacteria in food, and similar technology has also been employed to kill bacteria such as anthrax on or within pieces of mail.

However, this approach also has drawbacks in that such irradiation equipment has traditionally been costly. Moreover, the effectiveness of such irradiation equipment has been limited because articles such as pieces of mail may become contaminated with one or more of a variety of biological and/or chemical agents. For example, although irradiation equipment employing electron beam technology may be effective in killing anthrax spores, it may be incapable of destroying other biological contaminants such as HIV and E-Coli, and agents that cause, e.g., smallpox, influenza, plague, and botulism.

It would therefore be desirable to have a system and method of disinfecting and/or decontaminating articles such as pieces of mail. Such a system would be effective for disinfecting and/or decontaminating articles that have been exposed to diverse biological and/or chemical contaminants. It would also be desirable to have a disinfecting and/or decontaminating system that is compact, easy to use, and relatively low cost.

BRIEF SUMMARY OF THE INVENTION

In accordance with the present invention, a system and method is disclosed that is capable of disinfecting and/or decontaminating articles such as pieces of mail that have been exposed to diverse biological and/or chemical contaminants. The presently disclosed system employs various technologies such as radiation beam technology, electromagnetic field technology, ultraviolet radiation technology, chemical decontamination technology, and suitable combinations of these technologies to provide effective disinfection and/or decontamination of mail at the point of entry into the postal system and/or at the point of mail delivery.

In one embodiment, the system for disinfecting and/or decontaminating articles such as pieces of mail comprises a mail box processor including an enclosure having a door, at least one input port, and at least one output port, a mail tumbling drum, at least one radiation beam source and applicator, at least one electromagnetic field source and applicator, at least one ultraviolet radiation source and applicator, at least one chemical decontamination unit, and a status indicator.

In the presently disclosed embodiment, the enclosure door is opened, a quantity of mail including suitably sized letters and packages is placed in the mail tumbling drum inside the enclosure, and the door is closed. The status indicator then flashes a warning light indicating that the disinfection/decontamination process is to begin within a predetermined delay time. At the end of the predetermined delay time, radiation beams, electromagnetic fields, ultraviolet radiation, and chemical decontaminates are applied to the quantity of mail in the tumbling drum for a predetermined time, and in predetermined combinations and sequences. Further, the mail tumbling drum rotates at predetermined speeds and directions to assure that each piece of mail is fully exposed to the beams, fields, radiation, and chemical decontaminates, thereby destroying essentially all biological viruses, bacteria, spores, pollutants, and bomb material that may be on or within the pieces of mail. The input and output ports of the mail box processor enclosure are configured to minimize leakage so that contaminating substances harmful to humans and animals are contained and deactivated within the enclosure.

By providing a mail box processor that employs technologies such as radiation beam, electromagnetic field, ultraviolet radiation, and chemical decontamination technologies for disinfecting and/or decontaminating pieces of mail within a secure enclosure, harmful substances including diverse biological and/or chemical contaminants on or within the mail can be deactivated while minimizing health risks to individuals in the proximity of the device.

An embodiment of the invention includes an article processing apparatus. The article processing apparatus includes a housing defining an enclosure, a rotatable drum disposed in the enclosure, the rotatable drum defining a cavity, at least one opening in flow communication with the cavity, at least one door configured to cover the at least one opening and substantially prevent fluid flow therethrough, a heating apparatus configured to raise a temperature of the air in the cavity, a microwave apparatus configured to provide microwave energy to the cavity, a plurality of ultraviolet light emitting apparatuses configured to provide ultraviolet light to the cavity, and a chemical applicator configured to dispose a chemical in the cavity.

Various embodiments of the invention may include one or more of the following aspects: the housing may include a layer of amorphous magnesium silicate fiber; at least one belt configured to rotate the drum; the at least one opening may include at least two openings; a first of the at least two openings may be configured to allow articles to be placed in the cavity and the second of the at least two openings may be configured to allow articles to be removed from the cavity; the heating apparatus may be configured to raise a temperature of the air in the cavity to at least 120° C.; the heating apparatus may be configured to raise a temperature of the air in the cavity to at least 130° C.; the plurality of ultraviolet light emitting apparatuses may include at least two pulsed ultraviolet lights each configured to emit ultraviolet light at an intermittent rate and at least one constant ultraviolet light configured to emit ultraviolet light at a substantially constant rate; the plurality of ultraviolet light emitting apparatuses may be configured to emit ultraviolet light having a wavelength between about 190 nanometers and 2000 nanometers; the chemical applicator may be configured to form a mist of the chemical in the cavity; the chemical applicator may be configured to form atomized droplets of the chemical having a diameter on the order of 10 microinches; the chemical applicator may be configured to inject the chemical into the cavity; a plurality of latches configured to latch the at least one door to the housing; the article processing apparatus may be configured such that power cannot be supplied to any of the heat treatment apparatus, microwave apparatus, and the plurality of ultraviolet light emitting apparatuses unless the plurality of latches have securely latched the at least one door to the housing; a first of the plurality of latches may be a mechanical latch and the second of the plurality of latches may be a magnetic latch; the article processing apparatus may have a volume of less than about 9 cubic feet; and the article processing apparatus may be configured to be powered by a power source operating at up to about 20 amps, between about 110V and about 120V, and between about 50 Hz and 60Hz.

Another embodiment of the invention may include a vehicle. The vehicle includes any article processing apparatus described herein and a power source configured to provide power to the article processing apparatus.

A further embodiment of the invention may include a wall disposed between a first room and a second room. The wall may include any article processing apparatus described herein, with a first opening of the article processing apparatus in flow communication with both a first room and the cavity of the article processing apparatus, and a second opening of the article processing apparatus in flow communication with both a second room and the cavity of the article processing apparatus.

Yet another embodiment of the invention includes a method of decontaminating articles within an apparatus that includes a housing defining at least one opening, and an enclosure in flow communication with the at least one opening, at least one door configured to cover the at least one opening, respectively, and a rotatable drum in the enclosure, the rotatable drum defining a cavity. The method includes placing articles into the cavity via the at least one opening, confirming that the at least one door is latched to the housing, rotating the drum, heating the air in the cavity, providing microwave energy to the cavity, providing ultraviolet light to the cavity from a plurality of ultraviolet light emitting apparatuses, placing a chemical in the cavity, opening the at least one door, and removing the articles from the cavity via the at least one opening.

Various embodiments of the invention may include one or more of the following aspects: mechanically latching the at least one door to the housing; magnetically latching the at least one door to the housing; rotating the drum at a speed up to about 20 revolutions per minute; rotating the drum at a speed up to about 30 revolutions per minute; heating the air in the cavity to a temperature of at least 120° C.; heating the air in the cavity to a temperature of at least 130° C.; placing a chemical in the cavity after the air in the cavity has reached at least 130° C.; providing microwave energy to the cavity at a power output between about 500 Watts and about 1000 Watts and at a frequency of about 2.4 GHz; pulsing ultraviolet light into the cavity from a first of the plurality of ultraviolet light emitting apparatuses; providing ultraviolet light into the cavity from a second of the plurality of ultraviolet light emitting apparatuses at a substantially constant rate; providing ultraviolet light into the cavity at a wavelength between about 190 nanometers and about 2000 nanometers; forming a mist of the chemical in the cavity; forming atomized droplets of the chemical in the cavity having a diameter on the order of about 10 microinches; the chemical applicator may be configured to inject the chemical into the cavity; the at least one opening may be a first opening and a second opening; the articles may be placed in the cavity via the first opening and removed from the cavity via the second opening; and providing a vehicle including the housing defining the at least one opening, the at least one door, the drum, and a power source configured to operate at up to about 20 amps, between about 110V and about 120V, and between about 50 Hz and 60Hz.

A yet further embodiment of the invention may include an article processing apparatus. The article processing apparatus may include a housing defining an enclosure, a rotatable drum disposed in the enclosure, the rotatable drum defining a cavity, a holder configured to hold articles disposed in the cavity, at least one opening in flow communication with the cavity, at least one door configured to cover the at least one opening and substantially prevent fluid flow therethrough, a heating apparatus configured to raise a temperature of the air in the cavity, a microwave apparatus configured to provide microwave energy to the cavity, a plurality of ultraviolet light emitting apparatuses configured to provide ultraviolet light to the cavity, and a chemical applicator configured to dispose a chemical in the cavity.

Various embodiments of the invention may include one or more of the following aspects: the holder may be fixedly connected to the rotatable drum; the holder may include a plurality of portions configured to move relative to each other; the holder may be detachable from the rotatable drum; the holder may include a latch; the holder may be disposed in a central portion of the cavity; the holder may be disposed in a plane substantially parallel to a longitudinal axis of the rotatable drum; the holder may include perforations; and at least a portion of the holder may be made of a material configured to allow heat, air, microwave energy, ultraviolet light, and chemicals to flow therethrough.

Still another embodiment of the invention may include a method of decontaminating articles containing greater than 20% moisture by weight within an apparatus that includes a housing defining at least one opening, and an enclosure in flow communication with the at least one opening, at least one door configured to cover the at least one opening, respectively, and a rotatable drum in the enclosure, the rotatable drum defining a cavity. The method may include placing the articles in a water-based solution including a disinfectant, placing the articles into the cavity via the at least one opening, confirming that the at least one door is closed, rotating the drum, heating the air in the cavity, providing microwave energy to the cavity, providing ultraviolet light to the cavity from a plurality of ultraviolet light emitting apparatuses, placing a chemical in the cavity, opening the at least one door, removing the articles from the cavity via the at least one opening, and creating an electronic copy of the articles.

Various embodiments of the invention may include one or more of the following aspects: placing the articles in a holder; placing the holder in the drum; connecting the holder to the drum such that the holder is fixedly disposed relative to the drum; separating a first portion of the holder from a second portion of the holder; placing the articles between the first portion and the second portion; connecting the first portion and the second portion such that the first portion is fixedly disposed relative to the second portion; placing up to about one pound of articles in the holder; placing the holder in the drum; placing the articles in the cavity for about 50 minutes; and heating the air in the cavity to about 160° C.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE SEVERAL VIEWS OF THE DRAWING

The accompanying drawings, which are incorporated in and constitute a part of this specification, illustrate several embodiments of the invention and together with the description, serve to explain the principles of the invention.

DETAILED DESCRIPTION OF THE INVENTION

Reference will now be made in detail to the present embodiments of the invention, examples of which are illustrated in the accompanying drawings. Wherever possible, the same reference numbers will be used throughout the drawings to refer to the same or like parts.

A system and method of disinfecting and/or decontaminating articles such as pieces of mail is provided that can be deployed at the point of entry into the postal system, at the point of mail delivery, and/or at any other suitable location. The system for disinfecting and/or decontaminating articles comprises a mail box processor that employs various technologies such as radiation beam technology, electromagnetic field technology, ultraviolet radiation technology, chemical decontamination technology, and suitable combinations thereof to disinfect/decontaminate the mail, while minimizing health risks to the intended mail recipients and individuals in the proximity of the device.

Figure 1:
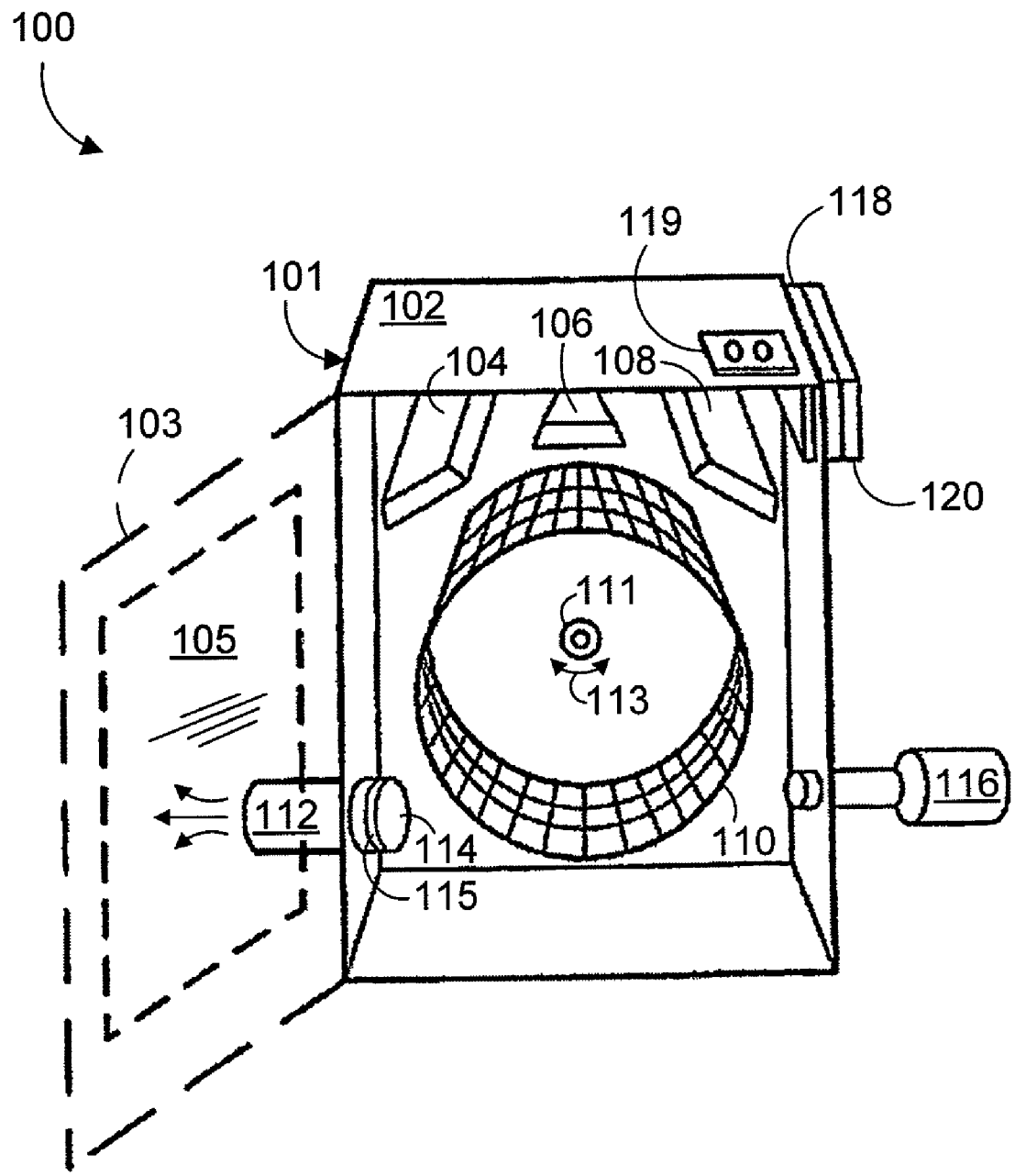
FIG. 1 is a perspective view of a mail box processor in accordance with the present invention.

FIG. 1 depicts an illustrative embodiment of a system for disinfecting and/or decontaminating mail, in accordance with the present invention. In the illustrated embodiment, the system 100 comprises a mail box processor 101 including an enclosure 102 with a door 103 (shown in phantom for clarity of illustration), a mail tumbling drum 110, a decontamination process in-progress/completed status indicator 119, an input port 120, and an output port 112. The mail box processor 101 further includes a radiation beam source and applicator 104, an electromagnetic field source and applicator 106, an ultraviolet ("UV") radiation source and applicator 108, and a chemical decontamination unit 116. It is understood, however, that in alternative embodiments, the mail box processor 101 may employ any other suitable disinfection/decontamination technology such as x-ray, gamma ray, broadband light beam, and oxidation technologies.

In the presently disclosed embodiment, the mail box processor 101 employs radiation beam technology, electromagnetic field technology, UV radiation technology, chemical decontamination technology, and/or suitable combinations of these technologies, for effectively disinfecting and/or decontaminating pieces of mail. To that end, a quantity of potentially contaminated mail is placed and confined in the mail tumbling drum 110 inside the enclosure 102, the enclosure door 103 is closed, and the mail in the tumbling drum 110 undergoes at least one disinfection/decontamination cycle using one or more of the above-mentioned technologies.

It is noted that the enclosure 102 including the door 103 is suitably shielded and gasketed to prevent leakage of electromagnetic and/or UV radiation during the disinfection/decontamination cycle. The enclosure 102 is further configured to prevent potentially harmful biological and/or chemical substances from escaping until the substances are either destroyed or otherwise rendered inactive by the decontamination process. As shown in FIG. 1, the enclosure door 103 includes a transparent section 105 to allow a human operator to observe the mail articles in the tumbling drum 110.

In the illustrated embodiment, the mail tumbling drum 110 is configured to allow radiation beams applied by the radiation beam applicator 104, electromagnetic fields applied by the electromagnetic field applicator 106, UV radiation applied by the UV radiation applicator 108, and chemical decontaminates applied by the chemical decontamination unit 116 to impinge upon the mail in the tumbling drum 110. For example, the mail tumbling drum 110 may have a mesh construction with suitably sized holes (not numbered). It is understood that the pieces of mail placed in the tumbling drum 110 include letters, packages, etc., suitably sized for placement and retention in the drum.

In the preferred embodiment, the mail tumbling drum 110 can handle at least 30 lbs. of mail during each disinfection/decontamination cycle. Further, the tumbling drum 110 is configured for rotationally oscillating about a hub 111, as depicted by directional arrows 113. The speed and direction of rotation of the mail tumbling drum 110 can be pre-set, e.g., pre-programmed, to assure that all portions of the mail are exposed to the applied radiation, electromagnetic fields, and/or chemical decontaminates. For example, the speed may be pre-set to a single speed, or pre-programmed to a number of varying speeds. Similarly, the direction of rotation may be pre-set to a single rotation direction, or pre-programmed to change direction a predetermined number of times. Moreover, all surfaces of the mail tumbling drum 110, and all internal surfaces of the enclosure 102 including the door 103, are preferably highly reflective to amplify the light ray disinfection energy applied to the mail during the decontamination process.

As described above, the enclosure 102 is configured to prevent potentially harmful biological and/or chemical substances (e.g., bacteria, bacteria spores, viral particles, and agents carrying viruses) inside the enclosure from escaping. To that end, the air pressure inside the enclosure 102 is made to be below atmospheric pressure. Specifically, the input port 120 is configured to allow ambient air to pass therethrough, and to enter the enclosure 102 via one or more orifices (not numbered). It is noted that a filter 118 may be employed to filter the ambient air before it enters the enclosure 102. The output port 112 is configured to draw the ambient air from the input port 120, through the inside of the enclosure 102, and back outside the enclosure 102, using, e.g., an air blower (not shown). As a result, even if there were any unwanted air leaks in the system 100, the air would simply be drawn into the enclosure 102 to be subsequently expelled through the output port 112.

As shown in FIG. 1, before the air inside the enclosure 102 re-enters the ambient environment via the output port 112, the air first passes through a filter 114, which in the presently disclosed embodiment is configured for capturing particulate matter. In the preferred embodiment, the first filter is a High Efficiency Particle Air (HEPA) filter capable of removing particles as small as approximately 1 pm (and/or between about 1 micron and 0.3 microns) from the air. A paper dust guard (not shown) may be disposed in front of the HEPA filter 114 to block any paper dust particles that may have released from the mail in the tumbling drum 110, thereby preventing the paper dust from filling the HEPA filter 114. Next, the air passes through a second filter 115, which is preferably a chemical filter capable of extracting desorbed chemicals from the air before it is expelled through the output port 112.

In the presently disclosed embodiment, the HEPA filter 114 and the chemical filter 115 are disposed within the enclosure 102 so that both of the filters 114-115 are exposed to the radiation beams, electromagnetic fields, UV radiation, and chemical decontaminates applied by the radiation beam applicator 104, the electromagnetic field applicator 106, the UV radiation applicator 108, and the chemical decontamination unit 116, respectively. In this way, the HEPA filter 114 and the chemical filter 115 are disinfected/decontaminated along with the mail during the decontamination process.

Figure 2:
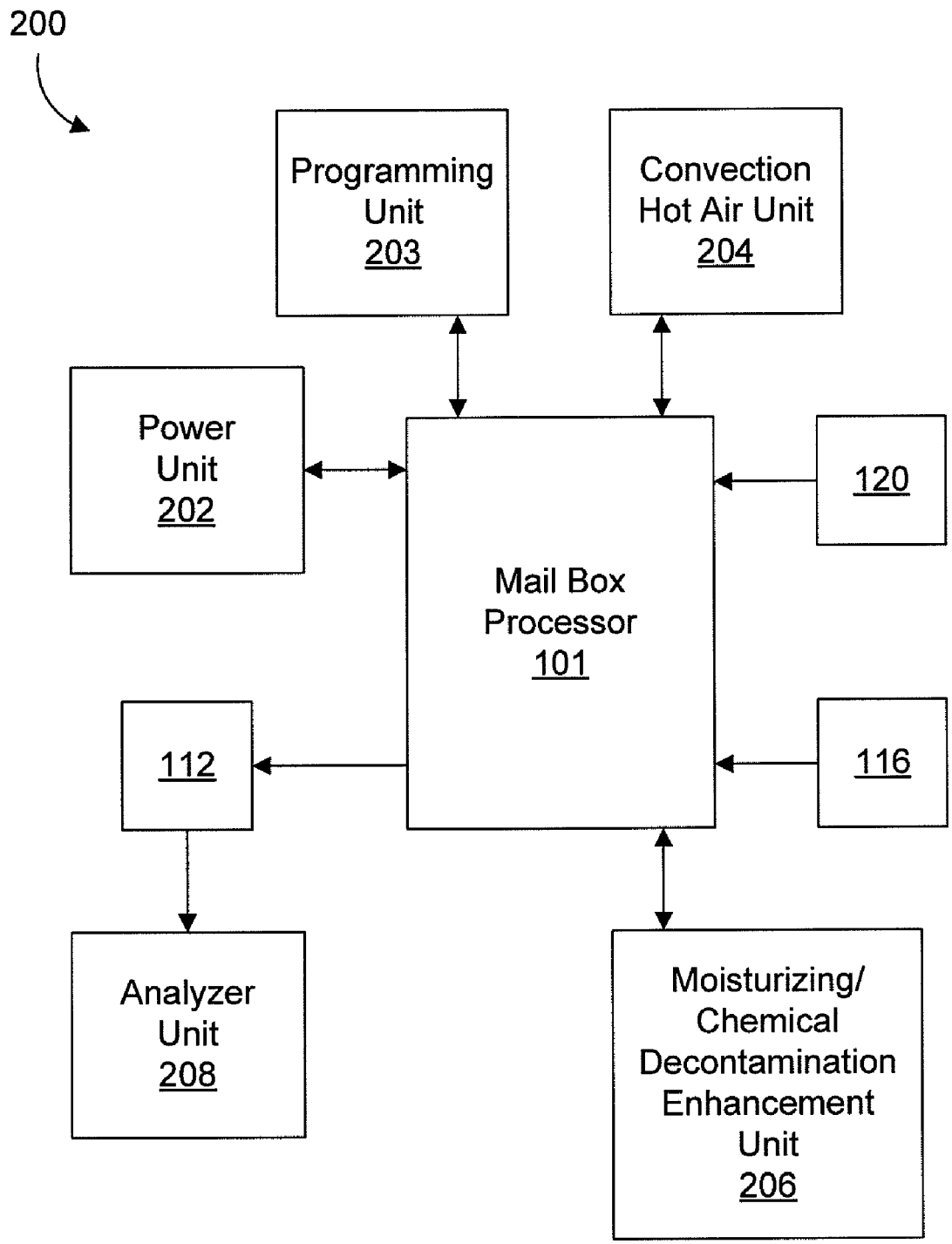
FIG. 2 is a block diagram of the mail box processor of FIG. 1.

FIG. 2 depicts a block diagram 200 of the system 100 for disinfecting and/or decontaminating mail (see FIG. 1). As shown in FIG. 2, the system 200 includes the mail box processor 101, the input and output ports 120 and 112, and the chemical decontamination unit 116. The system 200 further includes a power unit 202, a programming unit 203, a convection hot air unit 204, a moisturizing/chemical decontamination enhancement unit 206, and an analyzer unit 208.

In the preferred embodiment, the output port 112 includes a quartz tube (not numbered) through which the air inside the enclosure 102 (see FIG. 1) is expelled to the ambient environment. The analyzer unit 208 (see FIG. 2) is preferably operatively connected to the quartz tube for analyzing the expelled air to detect any harmful biological and/or chemical substances that might inadvertently escape from the mail box processor 101 during the decontamination process. For example, the quartz tube may be surrounded by an electromagnetic field to keep molecules within the tube suspended, thereby aiding in the subsequent analysis of the expelled air by the analyzer unit 208. Further, the analyzer unit 208 may employ one or more algorithms for removing background noise from selected DNA/RNA signals of specific molecular weights to aid in determining the species and origin of detected biological substances.

The convection hot air unit 204 is employed in conjunction with the input port 120 for optionally pre-heating the ambient air being drawn into the mail box processor 101. In alternative embodiments, the convection hot air unit 204 is also configured to provide infrared radiation disinfection capabilities that may be employed in conjunction with the radiation beam, electromagnetic field, and/or UV radiation applicators 104, 106, and 108 (see FIG. 1). For example, the electromagnetic field source and applicator 106 may be configured to apply microwave energy to the potentially contaminated mail in the tumbling drum 110. Because the mail may include metal objects such as staples or paper clips, the microwave energy and the infrared energy may be alternately applied to the mail by the electromagnetic field applicator 106 and the convection hot air unit 204, respectively, to reduce the chance of fire, which might occur if the microwave energy were continuously applied to the stapled pieces of mail during a typical decontamination process lasting 1-30 minutes. Further, by periodically pausing the application of the microwave energy, the power requirements of the mail box processor 101 can be reduced.

The moisturizing/chemical decontamination enhancement unit 206 is employed in conjunction with the chemical decontamination unit 116 (see FIG. 1) to produce an optimal disinfection chemical/moisture-based environment inside the mail box processor 101, thereby improving the effectiveness of the chemical decontamination portion of the disinfection/decontamination process. It is noted that the moisturizing/chemical decontamination enhancement unit 206 may also be employed to inject suitable chemicals, gas, and/or moisture inside the enclosure 102 (see FIG. 1) to prevent overheating of the enclosure contents, and further reduce the chance of fire within the mail box processor 101. For example, the moisturizing/chemical decontamination enhancement unit 206 may inject a chemical operative to eliminate oxygen from the enclosure 102.

Figure 3:
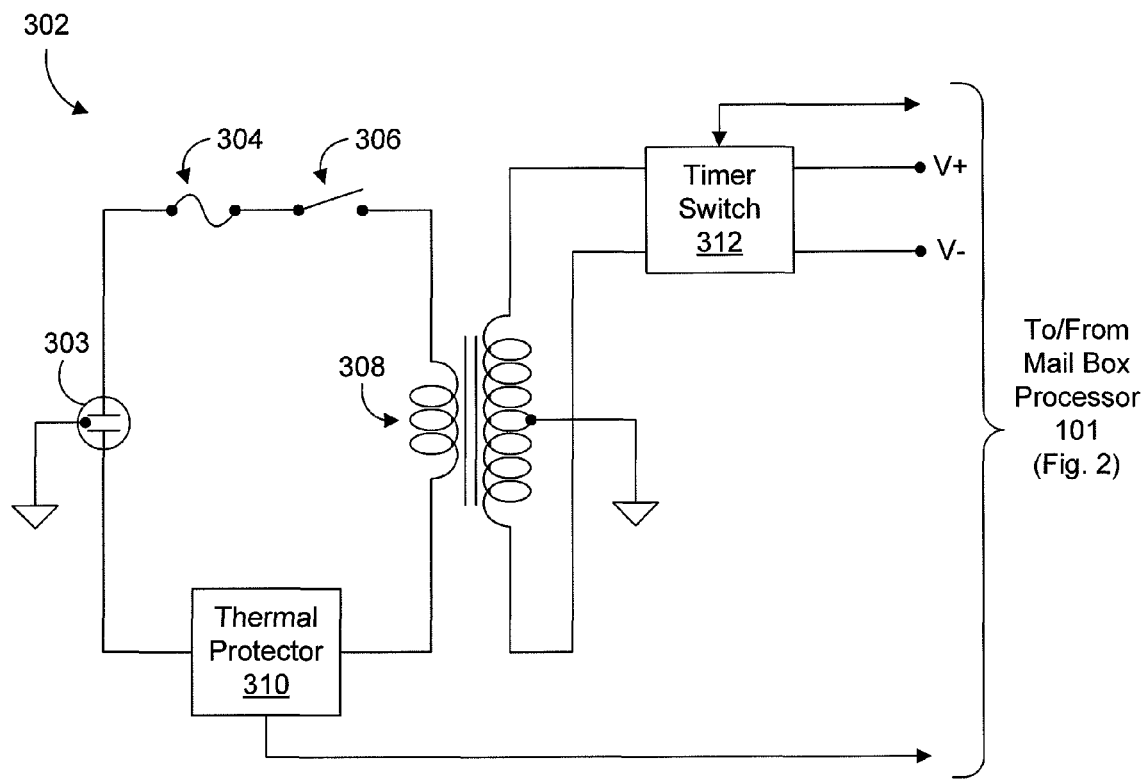
FIG. 3 is a schematic diagram of a power unit included in the mail box processor of FIG. 1.

FIG. 3 depicts an illustrative embodiment 302 of the power unit 202 (see FIG. 2). In the illustrated embodiment, the power unit 302 includes a connection 303 to line power, a fuse 304, a power switch 306, a transformer 308, a thermal protector 310, and a timer switch 312. For example, the specifications for the line power may be approximately 25 A, 120 V. As described above, the moisturizing/chemical decontamination enhancement unit 206 may be employed to inject suitable chemicals, gas, and/or moisture inside the enclosure 102 (see FIG. 1) to prevent overheating of the enclosure contents. The thermal protector 310 is configured to disconnect the power from the mail box processor 101 in the event the temperature inside the enclosure 102 exceeds a predetermined level. For example, the thermal protector 310 may comprise one or more Resistance Thermal Detectors (RTDs). In the preferred embodiment, the thermal protector 310 is further configured to convey status information to the mail box processor 101. Moreover, the timer switch 312 is configurable to provide power to the mail box processor 101 via power connections V+ and V− after a predetermined delay time. For example, the predetermined delay time may be pre-programmed in the timer switch 312 via the programming unit 203. The timer switch 312 is further configured to convey status information to the mail box processor 101.

As further described above, the speed and direction of rotation of the mail tumbling drum 110 may be pre-programmed, and the delay time provided by the timer switch 312 (see FIG. 3) may also be pre-programmed. To that end, the programming unit 203 comprises a suitable user interface, processor, and memory to enable the human operator to program these desired settings. Further, the programming unit 203 may be employed to execute appropriate disinfection/decontamination applications to assure that the radiation beams, electromagnetic fields, UV radiation, and chemical decontaminates are applied to the mail in the most effective intensities, combinations, and/or sequences for killing/destroying biological and/or chemical substances on or within the mail. For example, an appropriate decontamination process may include selectively activating/deactivating the chemical decontamination unit 116 to inject ozone into the enclosure 102, and then activating/deactivating the UV radiation applicator 108 to apply UV radiation to kill harmful bacteria on the mail. It is understood that the radiation beam applicator 104, and the electromagnetic field applicator 106, may also be activated and controlled via the programming unit 203.

It should be appreciated that the radiation beam source and applicator 104 of the mail box processor 101 (see FIG. 1) may be configured to provide an electron beam, or any other suitable radiation beam, having an intensity sufficient to kill harmful biological contaminants in mail disposed in the mail box processor 101. Further, the electromagnetic field source and applicator 106 may be configured to provide microwave, Radio Frequency (RF) wave, or any other suitable electromagnetic energy, and the UV radiation source and applicator 108 may be configured to provide UV radiation in the UV-C band, or any other suitable type of UV radiation, to kill the biological contaminants. Moreover, the chemical decontamination unit 116 may be configured to apply any suitable chemical decontaminates to rid the mail of chemical contamination. For example, the chemical decontamination unit 116 may employ one or more chemical bags to facilitate the application of the chemical decontaminates. It is further appreciated that the mail box processor 101 may be employed for disinfecting/decontaminating pieces of mail or any other suitable article.

Figure 4:
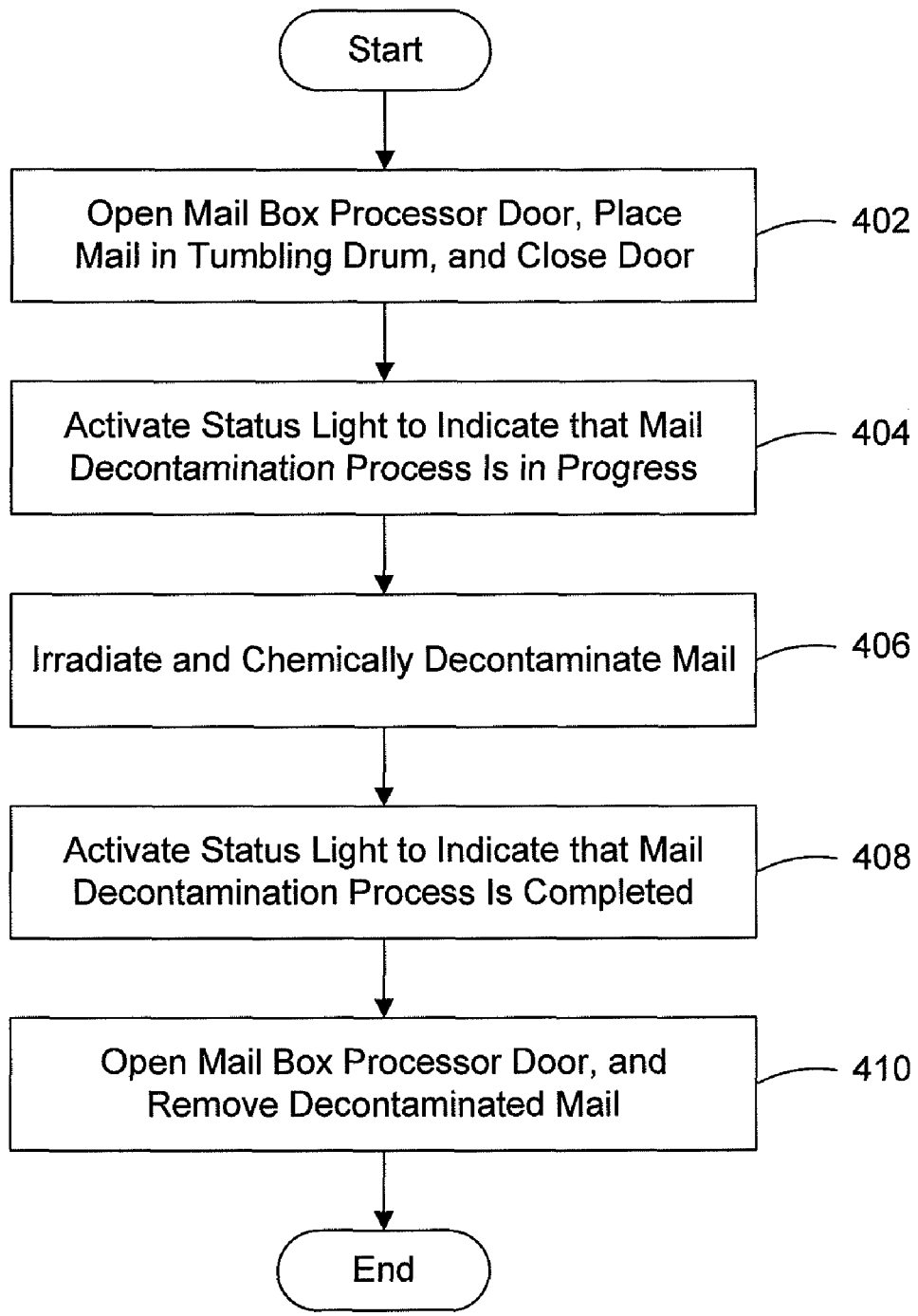
FIG. 4 is a flow diagram of a method of operation of the mail box processor of FIG. 1.
Figure 5A:
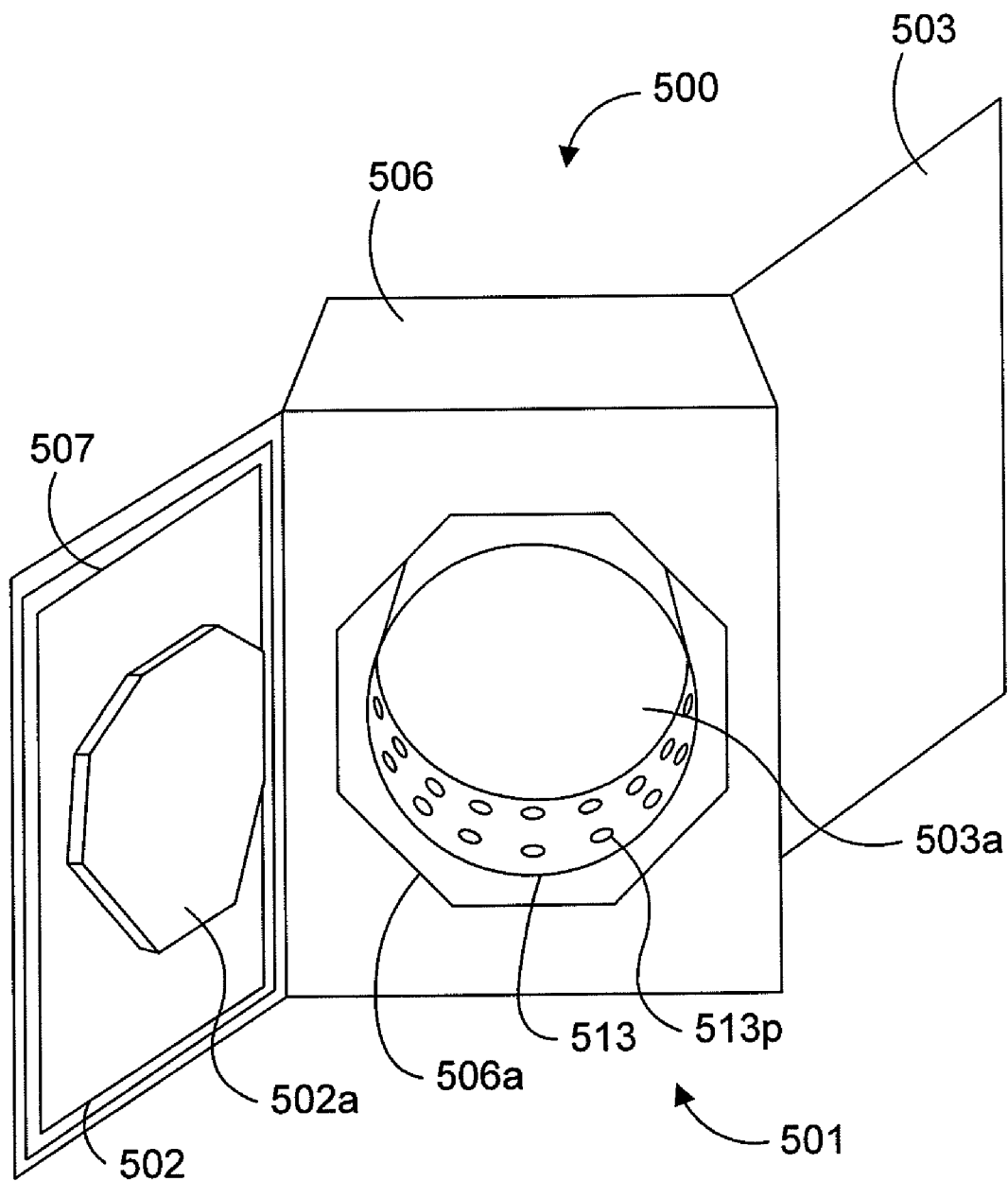
FIG. 5A is a perspective view of an articles processor in accordance with another embodiment of the present invention.
Figure 5B:
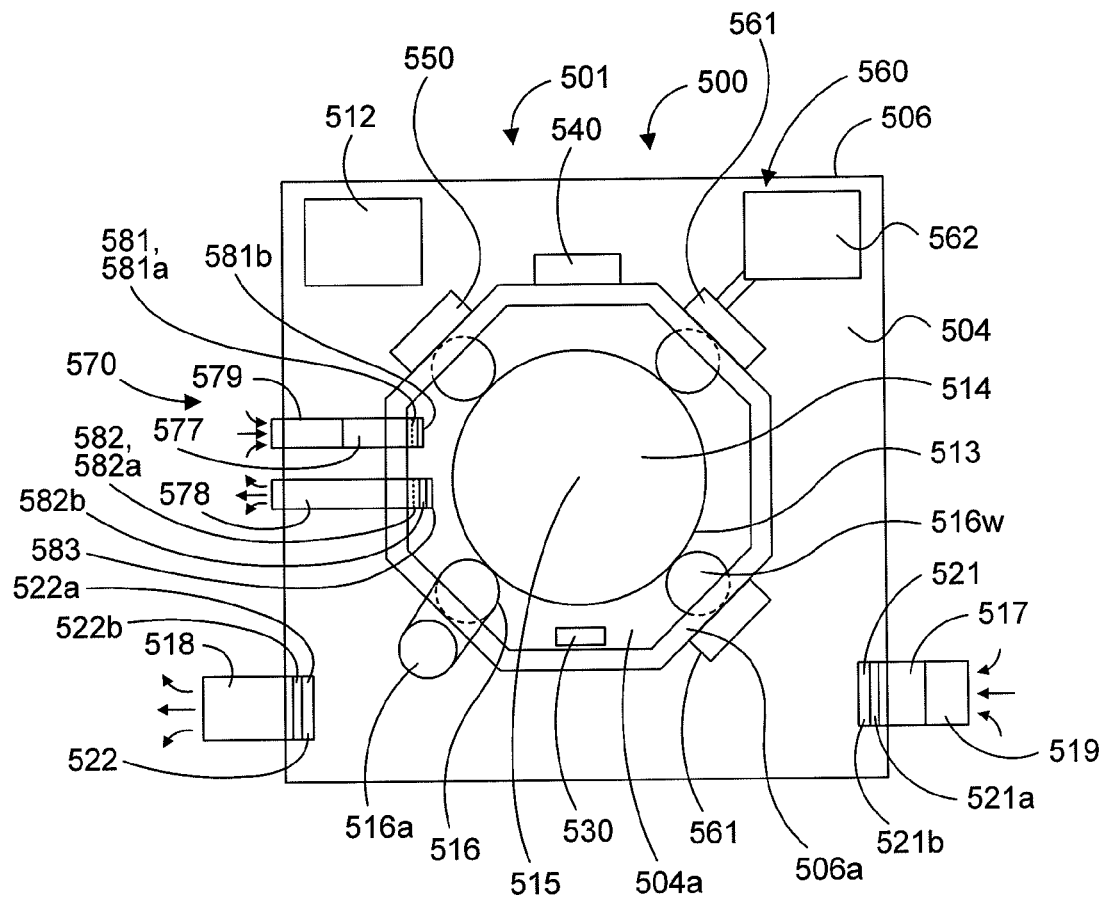
FIG. 5B is a side schematic view of the articles processor of FIG. 5A.
Figure 5C:
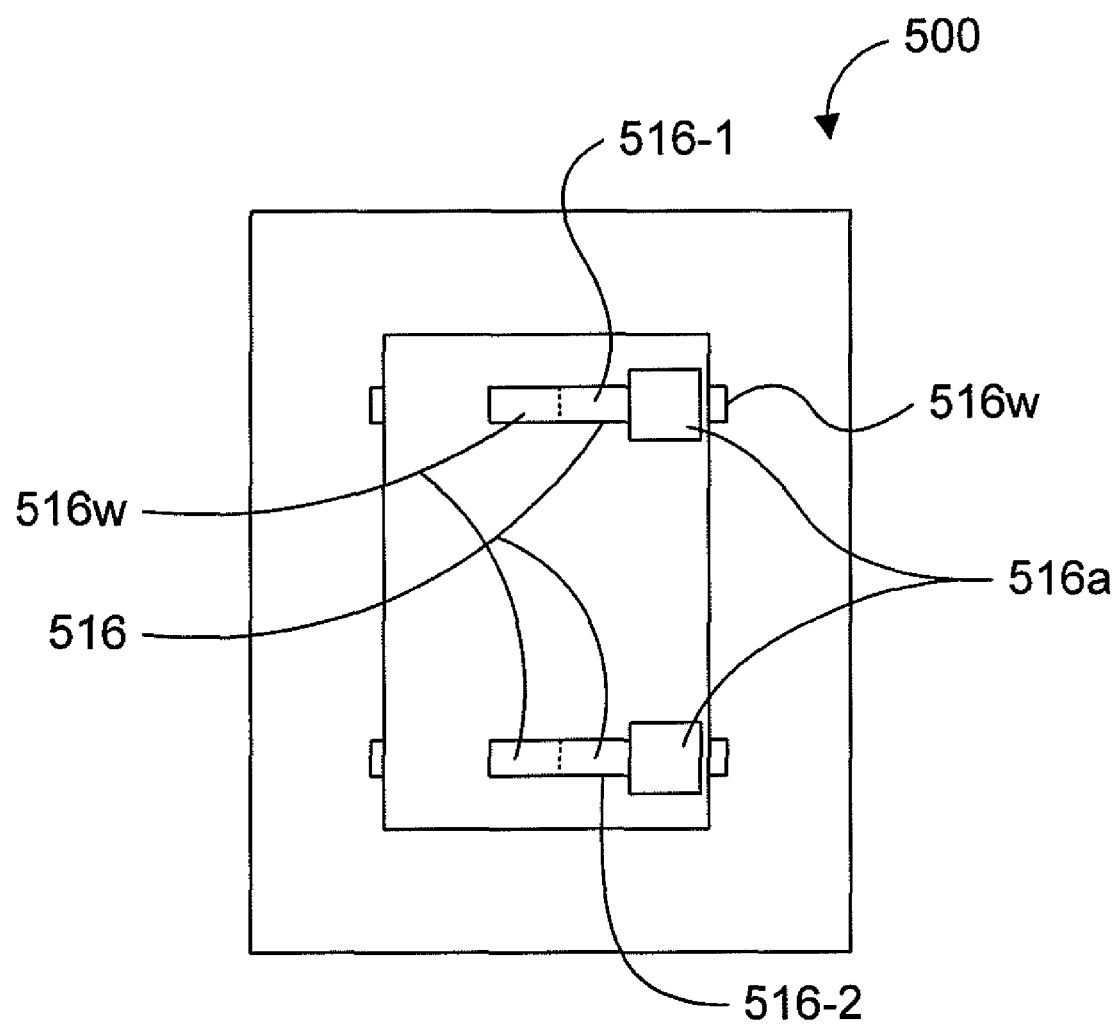
FIG. 5C is a top schematic view of the articles processor of FIG. 5A.
Figure 5D:
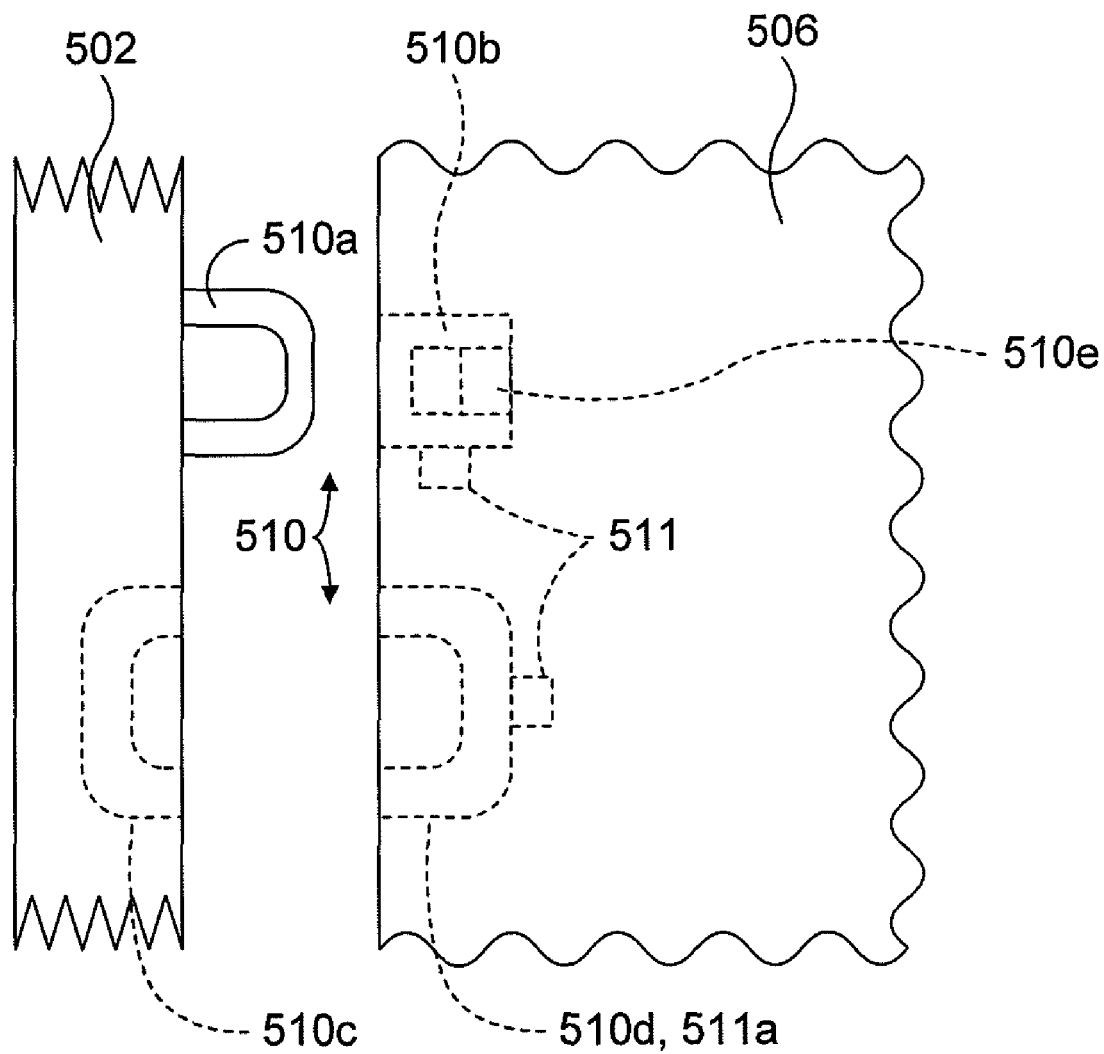
FIG. 5D is a schematic view of a portion of the articles processor of FIG. 5A.
Figure 5E:
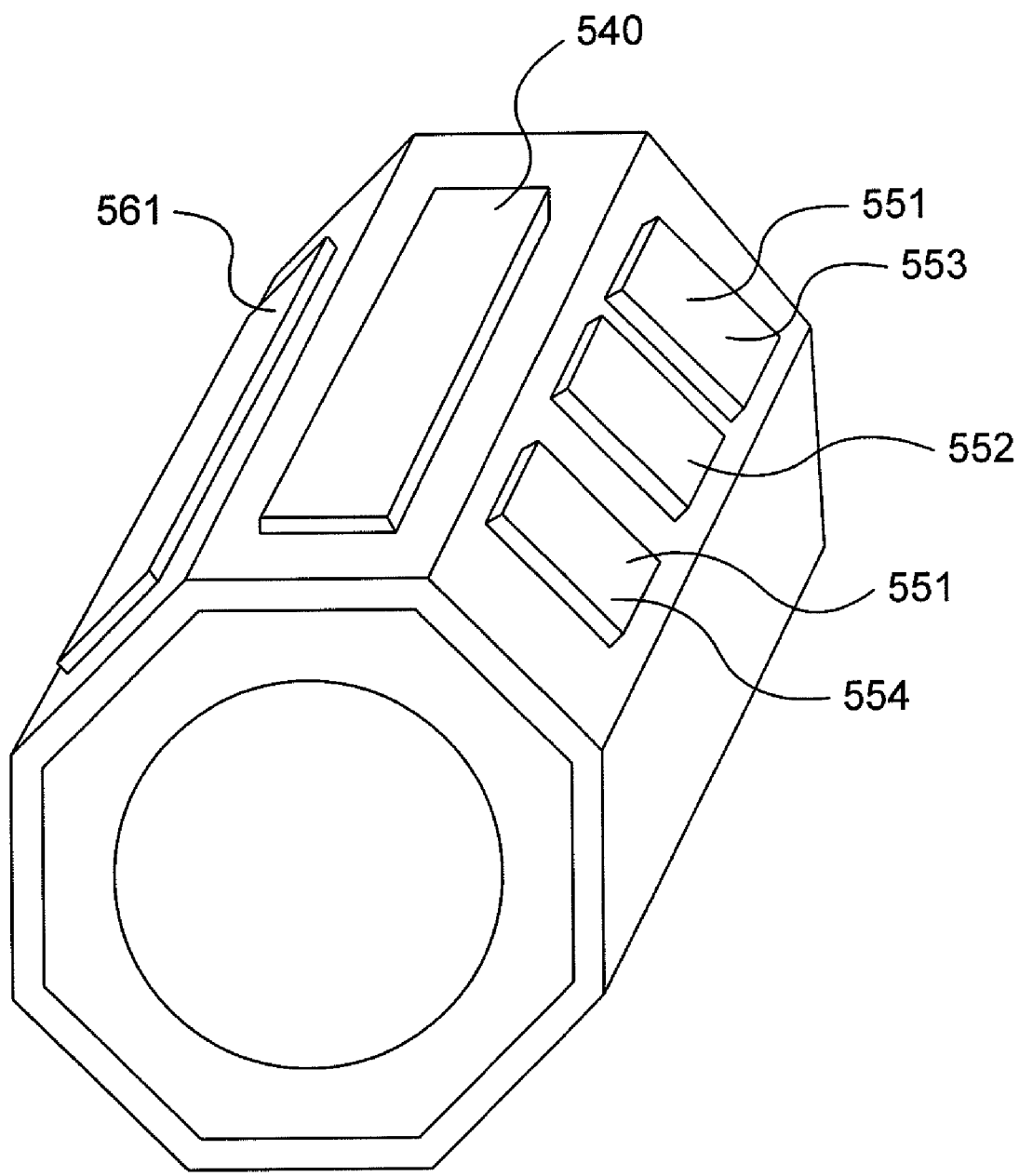
FIG. 5E is a schematic view of a portion of the articles processor of FIG. 5A.

A method of operating the presently disclosed mail box processor 101 (see FIG. 1) is illustrated by reference to FIG. 4. As depicted in step 402, the door is opened, a quantity of mail is placed in the tumbling drum, and the door is closed. Next, the status indicator "in-progress" light is activated, as depicted in step 404, to alert individuals in the proximity of the mail box processor that the mail decontamination process will be in-progress after the pre-programmed delay time, if any. The mail is then irradiated and chemically decontaminated, as depicted in step 406, via the radiation beam applicator, the electromagnetic field applicator, the UV radiation applicator, and the chemical decontamination unit. It is appreciated that the mail box processor is pre-programmed to apply the radiation and chemical decontaminates in the most effective intensities, combinations, and/or sequences for eliminating biological and chemical contaminates from the mail. At the end of the decontamination cycle, the status indicator "completed" light is activated, as depicted in step 408, to provide notification that the mail decontamination process is completed. The door of the mail box processor is then opened, as depicted in step 410, and the decontaminated mail is removed.

FIGS. 5A-5E depict an illustrative embodiment of a system for disinfecting and/or decontaminating articles (e.g., mail), in accordance with another embodiment of the present invention. The system 500 in FIGS. 5A-5E may have one or more of any of the features set forth herein, for example, one or more of the features associated with the illustrative embodiment set forth in FIG. 1. However, system 500 may also contain one or more features different from the features set forth herein, for example, one or more of the features associated with the illustrative embodiment set forth in FIG. 1.

System 500 may include an articles processor 501 including a housing 506 (e.g., including a frame), a first door 502, and a second door 503 which together define an enclosure 504. Each of housing 506, first door 502, and second door 503 may be configured to block the passage of radiation (e.g., microwave and/or ultraviolet) and/or contaminants (e.g., chemicals and/or biological agents) therethrough. For example, one or more of housing 506, first door 502, and second door 503 may be made out of stainless steel, aluminum, an insulating material, and/or any other material configured to block the passage of radiation and/or contaminants therethrough. One example of a suitable material is amorphous magnesium silicate fiber (AMSS). One such AMSS is sold under the tradename DYNAGUARD FLEXIBLE MICRO-POROUS INSULATION manufactured by THERMODYNE CORPORATION. Articles processor 501 may have a length of about 30 inches, depth of about 20.9 inches, and a height of about 31.38 inches First door 502, second door 503, and/or housing 506 that define enclosure 504 may include a layer of AMSS. Also or alternatively, a portion 506a of housing 506 defining a sub-enclosure 504a that includes drum 513 may include a layer of AMSS. Accordingly, the portion of housing 506, first door 502, and/or second door 503 defining sub-enclosure 504a may include a layer of AMSS. The layer of AMSS may have a thickness just sufficient to block passage of enough radiation from within enclosure 504 such that it is safe for a user to stand directly next to articles processor 501 without suffering ill effects from the radiation. For example, the layer of AMSS may be between about 0.5 inches and 0.25 inches thick. The thickness of the layer of AMSS may vary between first door 502, second door 503, and/or housing 506. The amount of AMSS used may be minimized, for example, because AMSS may be relatively expensive, and thus to minimize an overall cost of system 500.

The surfaces of doors 502, 503 defining enclosure 504 may be highly reflective, for example, to deflect and/or amplify the radiation applied to the articles during the decontamination process. Doors 502, 503 may also or alternatively include a protrusion 502a, 503a configured to extend into enclosure 504a, for example, about 1 inch. Protrusions 502a, 503a may form a gap between the 1 inch wide surface surrounding protrusion 502a, 503a and housing 506a. The gap may be configured to prevent microwaves or other waves (e.g., radiofrequency emissions and/or electromagnetic emissions) from exiting enclosure 504, 504a, for example, by dissipating the waves. For example, the gap may be configured to dissipate microwave emissions having a frequency of about 2.4 GHz. Protrusions 502a, 503a may be configured to dissipate waves without impeding airflow within enclosure 504a and/or cavity 514.

Housing 506, 506a, first door 502, and second door 503 may cooperate to prevent potentially harmful biological and/or chemical substances from escaping from enclosure 504, 504a at least until the substances are either destroyed or otherwise rendered inactive by the decontamination process. For example, one or more of first door 502 and second door 503 may each have a rubber gasket 507 lining an interface between each door 502, 503 and housing 506, 506a. Accordingly, gasket 507 may substantially prevent the passage of potentially harmful biological and/or chemical substances therethrough. Gasket 507 may also be configured to impede and/or prevent the passage of waves (e.g., microwaves, radiofrequency waves, and/or electromagnatic waves) through, for example, by having a metal component, such as aluminum, embedded therein.

Although housing 506, 506a, first door 502, and second door 503 may define an airtight enclosure for 504, 504a, such airtightness may not be necessary, for example, due to the presence of other portions of system 500 that will assist in preventing the escape of harmful biological and/or chemical substances from enclosure 504, 504a. In some embodiments, housing 506a, first door 502, and second door 503 may define a substantially airtight enclosure 504a, while housing 506, first door 502, and second door 503 may define an enclosure 504 that is not airtight.

One of first door 502 and second door 503 may be configured as a "clean" door (e.g., configured to remove decontaminated materials) while the other first door 502 and second door 503 may be configured as a "dirty" door (e.g., configured to receive contaminated materials). For example, articles or other articles may be exclusively placed into enclosure 504 via an opening configured to be covered by first door 502, and may be exclusively removed from enclosure 504 via an opening configured to be covered by second door 503. This may be desirable, for example, to make it more difficult (if not impossible) for articles or other articles being placed into enclosure 504 from contaminating articles or other articles being taken out of enclosure 504.

One of first door 502 and second door 503 may include a transparent section to allow a human operator to observe the articles in enclosure 504. Transparent section may be composed of plexiglas, plastics, ceramics or any other suitable material to allow a user to observe the inside of articles processor 501, but still protect the user from radiation, contaminants, and/or other potential harmful items present in enclosure 504.

First door 502 and second door 503 may be connected to housing 506 via any suitable means. For example, one side of each of first door 502 and second door 503 may be connect to housing 506 via a hinge. Each of first door 502 and second door 503 may be closed via a latch 510. Latch 510 may be any suitable latch (e.g., mechanical and/or magnetic). Other latches and latch configurations are also contemplated. One or more of housing 506, first door 502, and second door 503 may include a sensor 511 (e.g., mechanical and/or magnetic) configured to determine whether first door 502 and/or second door 503 is properly latched to housing 506 such that the opening in the housing 506 covered by respective door 502, 503 is closed. This may be desirable, for example, so that no harmful amount of radiation and/or contaminants leaves enclosure 504, 504a via the opening defined by the respective door 502, 503.

Latch 510 may include a protrusion 510a and aperture 510b, with one of protrusion 510a and aperture 510b disposed on door 502, 503 while the other of protrusion 510a and aperture 510b is disposed on housing 506. Protrusion 510a may be configured to be fit within aperture 510b. Protrusions 510a may be fixed in aperture 510b, for example, by a solenoid 510e such that door 502, 503 cannot be opened if protrusions 510a is fixed in aperture 510b via solenoid 510e. Solenoid 510e may be configured to keep protrusion 510a locked in aperture 510b even if power is cut off from article processor 501. Sensor 511 may be configured to detect whether protrusions 510a has been placed in aperture 510b (for example, by determining the position of solenoid 501e), thus indicating whether or not door 502, 503 has been properly closed. Latch 510 may also or alternatively include a pair of magnets 510c, 510d. One of magnets 510c, 510d may be disposed on housing 506 while the other of magnets 510c, 510d may be disposed on door 502, 503. One or more of magnets 510c, 510d may be polarized such that unless properly polarized ends of one magnet 510c are placed against properly polarized ends of the other magnet 510d, sensor 511 will not provide an indication that door 502, 503 has been properly closed.

In another example, magnet 510d may actually be a sensor 511a. Sensor 511a may or may not be magnetic itself. In such a case, article processor 501 may be configured such that sensor 511a is sensitive as to the exact position of the poles of magnet 510c. Accordingly, unless each proper pole of magnet 510c is placed on the proper portion of sensor 511a, sensor 511a will provide an indication the processor that door 502, 503 is open and/or will not provide an indication to processor 512 that door 502, 503 is closed. Thus, misalignment between at least one of the poles of magnet 510c and the proper portions of sensor 511a, even doors 502, 503 appear to be closed, may prevent power from being provided to portions of article processor 501.

Sensor 511 may be operatively connected to a processor 512 that receives information from sensor 511 as to whether one or more of doors 502, 503 is closed. Processor 512 may take that information and display it on a display panel 513 disposed on articles processor 501 and/or prevent the decontamination process from proceeding. For example, processor 512 may prevent radiation and/or chemicals from being introduced onto articles (e.g., articles) disposed within enclosure 504, 504a. In another example, while system 500 is running, processor 512 may prevent the doors 502, 503 from opening, for example, by keeping latch 510 in its locked configuration, regardless of outside intervention. In the event that power is purposefully or inadvertently cut off from portions of articles processor 501, processor 512 and latches 510 may prevent doors 502, 503 from being opened until power is restored to articles processor 501. In a further example, processor 512 control the power provided to portions of articles processor 501. Accordingly, if sensor 511 indicates to processor 512 that one or more of doors 502, 503 is not properly closed and/or latched, processor 512 may prevent power from flowing to one or more portions of articles processor 501. Processor 512 may be configured to run articles processor 501 with a minimum amount of software, for example, to simplify its operation and prevent bugs from causing articles processor 501 from running in an unsafe manner. Processor 512 may be configured to determine whether there is sufficient chemicals in chemical reservoir 562 to run a single articles processing cycle. If there is not sufficient chemicals in chemical reservoir 562, processor 512 may prevent articles processor 501 from operating.

An article tumbling drum 513 may be disposed within enclosure 504, 504a. Articles tumbling drum 513 may be substantially cylindrical in shape and may be configured and/or sized for articles (e.g., articles including letters and/or packages) to be placed within a central cavity 514 of drum 513. For example, drum 513 may be configured to handle at least 30 lbs of articles. In some embodiments, however, drum 513 may handle no more than about 8-12 lbs (or about 3.6-5.4 kilograms) of articles per cycle, and possibly no more than about 3 lbs to about 5 lbs per cycle. Articles processor 501 and drum 513 may be configured to handle articles having a maximum size of about 16 inches by 11.5 inches by 3.5 inches (or about 416 millimeters by 292 millimeters by 89 millimeters). However, in some embodiments articles processor 501 may be configured to handle first class mail, for example, a two sheet letter in a standard paper envelope. Drum 513 may have a diameter of about 15-16 inches, a length of about 18 inches, and a volume of about 2.5 cubic feet.

Drum 513 may be configured to allow radiation(s) and/or chemical(s) to impinge upon articles disposed in cavity 514 of drum 513. For example, drum 513 may have a substantially mesh-like construction with perforations 513p sized to allow chemical(s) to enter central cavity 514 and effectively coat the articles (i.e., sufficiently coat the articles such that the radiation(s) can penetrate the articles enough so as to substantially disinfect and/or decontaminate the articles. To that effect, drum 513 may include a plurality of perforations 513p. Some of the perforations 513p may be substantially the same size, while other perforations 513p may have different sizes.

Perforations 513p may be configured to allow radiation(s) (e.g., heat) and/or chemical(s) from outside of drum 513 to enter cavity 514, and may also or alternatively be configured to impede the movement of the radiation(s) and/or chemical(s) out of cavity 514. In another example, drum 513 may be made of a material configured to allow radiation(s) and/or chemical(s) to impinge upon articles disposed in cavity 514 of drum 513. One or more surfaces of drum 513 may include (e.g., be made of and/or coated with) a highly reflective material (e.g., polished metal), for example, to amplify radiation applied to the articles during the decontamination process.

Drum 513 is configured to rotate about an axis 515, for example, via one or more belts 516. One or more of belts 516 may be rotated via an actuator 516a, and such rotation may be imparted to drum 513 via belts 516 rotating wheels 516w. For example, drum 513 may be rotated by two belts 516-1, 516-2. Drum 513 may be rotated by two belts 516-1, 516-2, for example, such that all portions of drum 513 rotate at a more balanced rate and/or more evenly distribute the stress exerted by belts 516-1, 516-2 on drum 513. Wheels 516w may be disposed around drum 513. Wheels 516w may be powered (e.g., via actuator 516a and/or belts 516-1, 516-2) or unpowered and may be configured about 513 so as to allow drum 513 to rotate smoothly and/or evenly. Actuator 516a may be a motor manufactured by DAYTON, however, any suitable motor configured to drive belts 516 is contemplated. Actuators 516a may be chosen because they are reliable, require little maintenance, are quiet, and/or are inexpensive.

Belts 516 and actuator 516a may be configured to rotate drum 513 at variable speeds and in variable directions. The speed and direction of the rotation of the drum 513 may be pre-determined (e.g., pre-programmed), for example, to ensure that all portions of the articles are sufficiently exposed to the applied radiation and/or chemicals so as to be disinfected and/or decontaminated. For example, the speed may be pre-set to a single speed, or pre-programmed to a number of varying speeds. Similarly, the direction of rotation may be pre-set to a single rotation direction, or pre-programmed to change direction a predetermined number of times. In a preferred embodiment, drum 513 is rotated at a speed of about 20 revolutions per minute in one direction. However, any suitable speed and/or changes in direction are contemplated. For example, drum 513 may be rotated at a speed of about 30 revolutions per minute.

Articles processor 501 may include a fluid exchange system 520 (e.g., air exchange system). Fluid exchange system 520 may be configured to cool processor 512 and/or other components disposed inside enclosure 504 and/or outside enclosure 504a. Fluid exchange system 520 may include a fluid inlet 517 and a fluid outlet 518 disposed on a portion of housing 506, and a fluid pump 519 coupled to one of fluid inlet 517 and fluid outlet 518. Fluid inlet 517 may be configured to allow a fluid (e.g., ambient air) to pass therethrough and to enter enclosure 504. Fluid inlet 517 may also be configured to allow fluid to pass therethrough in only one direction (e.g., fluid inlet 517 may allow fluid only to enter enclosure 504 from the outside environment via a one-way valve). Fluid inlet 517 may include a fluid filter 521 configured to filter fluid (e.g., ambient air) from the outside environment prior to the fluid entering enclosure 504. Fluid outlet 518 may be configured allow a fluid (e.g., air) to pass therethrough and to exit enclosure 504. Fluid outlet 518 may also be configured to allow fluid to pass therethrough in only on direction (e.g., fluid outlet 518 may allow fluid only to exit enclosure 504 to the outside environment via a one-way valve). Fluid outlet 518 may include a fluid filter 522 configured to filter fluid (e.g., air) from enclosure 504 prior to the fluid exiting enclosure 504 to the outside environment.

Fluid filter 521, 522 may each include one or more filters. For example, fluid filter 521, 522 may include at least one microbial filter 521a, 522a. Fluid filter 521, 522 may also or alternatively each include at least one carbon (e.g., charcoal) filter 521b, 522b (e.g., configured to remove odor) that may be disposed on one side of microbial filter 521a, 522a. For example, at least one carbon filter 521b, 522b may be disposed on the side of microbial filter 521a, 522a facing enclosure 504. Each fluid filter described herein may require periodic replacing, for example, because their filtering effectiveness has been reduced due to usage over time.

Fluid pump 519 (e.g., a fan) may be coupled to one of fluid inlet 517 and fluid outlet 518. If fluid pump 519 is coupled to fluid inlet 517, fluid pump 519 may be configured to draw fluid from the outside environment into enclosure 504. If fluid pump 519 is coupled to fluid outlet 518, fluid pump 519 may be configured to draw fluid from inside enclosure 504 to the outside environment. Fluid pump 519 may pump fluid before or after the fluid has passed through one or more filters 521, 522. Accordingly, fluid pump 519 may pump fluid from the outside environment, through fluid inlet 517, through filter 521, through enclosure 504, through filter 522, through fluid outlet 518, and to the outside environment. Fluid pump 519 lessens the need for enclosure 504 to be airtight, as even if there were any unwanted air leaks in enclosure 504, the fluid would simply be drawn into enclosure 504 and subsequently expelled through fluid outlet 518. Thus, no contaminated fluid would exit enclosure 504 other than via fluid outlet 518.

Articles processor 501 may include an inner fluid exchange system 570 (e.g., air exchange system). Fluid exchange system 570 may include a fluid inlet 577 and a fluid outlet 578 disposed on a portion of housing 506a, and a fluid pump 579 coupled to one of fluid inlet 577 and fluid outlet 578. Fluid inlet 577 may be configured to allow a fluid (e.g., ambient air) to pass therethrough and to enter enclosure 504a and/or cavity 514. Fluid inlet 577 may also be configured to allow fluid to pass therethrough in only one direction (e.g., fluid inlet 577 may allow fluid only to enter enclosure 504a from the outside environment via a one-way valve). Fluid inlet 577 may include a fluid filter 581 configured to filter fluid (e.g., ambient air) from the outside environment prior to the fluid entering enclosure 504a. Fluid outlet 578 may be configured allow a fluid (e.g., air) to pass therethrough and to exit enclosure 504a. Fluid outlet 578 may also be configured to allow fluid to pass therethrough in only on direction (e.g., fluid outlet 578 may allow fluid only to exit enclosure 504a to the outside environment via a one-way valve). Fluid outlet 578 may include a fluid filter 582 configured to filter fluid (e.g., air) from enclosure 504a prior to the fluid exiting enclosure 504a to the outside environment.

Fluid filter 581, 582 may each include one or more filters. For example, fluid filter 581, 582 may include at least one microbial filter 581a, 582a (e.g., configured to remove microbes). Fluid filter 581, 582 may also or alternatively each include at least one carbon (e.g., charcoal) filter 581b, 582b (e.g., configured to remove odor) that may be disposed on one side of microbial filter 581a, 582a. For example, at least one carbon filter 581b, 582b may be disposed on the side of microbial filter 581a, 582a facing enclosure 504a. Each fluid filter described herein may require periodic replacing, for example, because their filtering effectiveness has been reduced due to usage over time.

Fluid outlet 578 may also include a filter 583 configured to prevent microwave or other waves (e.g., radiofrequency or electromagnetic) from exiting enclosure 504a via fluid outlet 578, for example, by dissipating the waves. For example, filter 583 may be made out of aluminum and may be a honeycomb like structure having cells where each side of the hexagon is about ⅛ of an inch. However, filter 583 may include structures having any suitable geometric shape, for example, a plurality of parallel cylinders. Filter 583 may be about ¼ of an inch thick. Filter 583 may be configured to dissipate microwaves having a frequency of about 2.4 GHz. Filter 583 may be disposed upstream and/or downstream from one or more filters 582a, 582b.

Fluid pump 579 (e.g., a fan) may be coupled to one of fluid inlet 577 and fluid outlet 578. If fluid pump 579 is coupled to fluid inlet 577, fluid pump 579 may be configured to draw fluid from the outside environment into enclosure 504a. If fluid pump 579 is coupled to fluid outlet 578, fluid pump 579 may be configured to draw fluid from inside enclosure 504a to the outside environment. Fluid pump 579 may pump fluid before or after the fluid has passed through one or more filters 581, 582. Accordingly, fluid pump 579 may pump fluid from the outside environment, through fluid inlet 577, through filter 581, through enclosure 504a, through filters 582, 583, through fluid outlet 578, and to the outside environment. Fluid pump 579 lessens the need for enclosure 504a to be airtight, as even if there were any unwanted air leaks in enclosure 504a, the fluid would simply be drawn into enclosure 504a and subsequently expelled through fluid outlet 578. Thus, no contaminated fluid would exit enclosure 504a other than via fluid outlet 578. Fluid inlet 577 and fluid outlet 578 may be located on any portion of articles processor 501. For example, fluid inlet 577 may run between the top or side of articles processor 501 and enclosure 504a, while fluid outlet 578 may run between enclosure 504a and the bottom of articles processor 501.

Articles processor 501 may include a plurality of decontamination units. For example, articles processor 501 may be configured to destroy biological contaminants and/or neutralize chemical contaminants through a combination of one or more of a heat treatment, a microwave treatment, an ultraviolet light treatment, and a chemical solution.

Heat may be applied to articles disposed in cavity 514 via a heat treatment apparatus 530. Heat treatment apparatus 530 may be disposed within enclosure 504, 504a, outside drum 513, and/or inside enclosure 506a. Heat treatment apparatus 530 may be about 12 inches in length and may be disposed substantially below drum 513 in a direction substantially parallel to the axis of rotation of drum 513. Perforations 513p may be configured to allow heat from heat treatment apparatus 530 disposed outside of drum 513 to enter cavity 514, and may also or alternatively be configured to impede the movement of heat out of cavity 514. A combination of the rotating of drum 513 and/or perforations 513 may assist in circulating the heat throughout cavity 514. The operation of heat treatment apparatus 530 may be controlled by processor 512, which may prevent heat treatment apparatus 530 from being powered if doors 502, 503 are not properly closed.

Heat treatment apparatus 530 may be configured to provide a range of heat sufficient to destroy biological contaminants and/or denature at least some chemical contaminants. For example, heat treatment apparatus 530 may be configured to heat the space within enclosure 504, 504a between about 250° F. and about 320° F. (and/or between about 120° C. and about 150° C.) at about 1000 Watts. In various embodiments, however, heat treatment apparatus 530 may be configured to heat the space within enclosure 504, 504a up to about 240° C. (e.g., up to about 180° C. and/or up to about 200° C.) at any suitable wattage. During a single cycle, heat treatment apparatus 530 may be configured to apply heat to the articles for about 30 minutes or substantially the entire length of the cycle. Heat treatment apparatus 530 may be configured to control the temperature in enclosure 504 within a tolerance of about 2 percent.

Microwave energy may be applied to articles disposed in drum 513 in enclosure 504 via a microwave apparatus 540. Microwave apparatus 540 may be disposed within enclosure 504 and outside drum 513. In various embodiments, microwave apparatus 540 may be disposed inside and/or outside of housing 506a defining enclosure 504a. Drum 513, perforations 513p, and/or enclosure 506a may be configured to allow microwave energy from microwave apparatus 540 to pass therethrough so as to impinge on articles disposed in the space defined by drum 513. Microwave energy from microwave apparatus 540 may be configured to excite liquid(s), chemical(s), and/or objects disposed in the space defined by drum 513, for example, to at least assist in generating heat, destroying biological contaminants, neutralizing chemical contaminants, alter the genetic composition/makeup of the biological contaminant, and/or sterilize the biological contaminant.

Microwave apparatus 540 may be configured to provide a range of microwave energy sufficient to destroy at least some biological contaminants and/or denature at least some chemical contaminants. For example, microwave apparatus 540 may be configured to provide microwave energy to the articles disposed in drum 513 at a power of between about 500 Watts and about 1000 Watts at a frequency of about 2.4 GHz. During a single cycle, microwave apparatus 540 may be configured to apply heat to the articles for about 30 minutes or substantially the entire length of the cycle.

Ultraviolet light may be applied to articles disposed in drum 513 in enclosure 504 via at least one ultraviolet light apparatus 550. At least one ultraviolet light emitting apparatus 550 may be disposed within enclosure 504 and outside drum 513, and may also or alternatively be disposed inside and/or outside housing 506a and/or enclosure 504a. The at least one ultraviolet light emitting apparatus 550 may include a first ultraviolet light emitting apparatus 551 and a second ultraviolet light emitting apparatus 552.

Ultraviolet light emitting apparatus 550, 551, 552 may each be configured to provide a range of ultraviolet light sufficient to destroy biological contaminants and/or neutralize at least some chemical contaminants. First ultraviolet light emitting apparatus 551 and second ultraviolet light emitting apparatus 552 may have substantially the same technical characteristics or may have substantially different technical characteristics, for example, to destroy and/or neutralize a wider range of contaminants. Ultraviolet light emitted by each of first ultraviolet light emitting apparatus 551 and second ultraviolet light emitting apparatus 552 may be configured to interact with liquid(s) and/or chemical(s) present in cavity 514 so as to more effectively destroy and/or neutralize contaminants, for example, by penetrating an outside layer of a first class letter so as to destroy and/or neutralize contaminant that may be contained therein.

For example, first ultraviolet light emitting apparatus 551 may have two pulsed lights 553, 554 that each emit a pulsed ultraviolet light at about 60 Watts, at a frequency of about 50 Hz, and/or a wavelength of between about 190 nanometers and about 2000 nanometers. Such a pulsed light may be effective in destroying and/or neutralizing a first set of contaminants. First ultraviolet light emitting apparatus 551 may have two pulsed lights 553, 554 arrange about drum 513 such that the pulsed ultraviolet light is more evenly distributed about within cavity 514 than if there were only one pulsed light.

In another example, second ultraviolet light emitting apparatus 552 may emit a constant ultraviolet light at about 150 microwatts per square centimeter, at a frequency of about 50 Hz, and/or a wavelength between about 249 nanometers and about 254 nanometers. Such a constant light may be effective in destroying and/or neutralizing a second set of contaminants substantially the same as or different from the first set of contaminants.

At least one chemical may be applied to articles disposed in drum 513 in enclosure 504 via one or more chemical applicators 560. Chemical applicators 560 may include one or more nozzles 561 (e.g., two nozzles) in fluid connection with a chemical reservoir 562.

Chemical reservoir 562 may have a capacity of about one gallon. One article processing cycle may use about ½ cup (about 4 fluid ounces) of chemical. However, more or less chemical may be used depending on the type of biological contaminant that needs to be destroying and/or the type of chemical contaminant that needs to be neutralized.

Processor 512 may control nozzle(s) 561 so as to control the chemical flow into enclosure 504 and/or drum 513. Nozzle(s) 561 may be configured to apply a chemical from chemical reservoir 562 into enclosure 504 in a manner so as to maximize the effectiveness of the chemical. For example, nozzle(s) 561 may be configured to create a mist in enclosure 504 in a sufficient amount to coat the articles disposed in enclosure 504a, drum 513, and/or penetrate the articles. In some embodiments, the droplets of chemical(s) disposed in drum 513 may have a diameter of about 1 microinches. In another example, nozzle(s) 561 may be disposed around drum 513 at about a 70 degree angle relative to a vertical plane that includes the longitudinal axis of drum 513. Nozzle(s) 561 may be disposed on different sides of drum 513 and may be connected to housing 506a. Each nozzle 561 may include an array of openings each configured to expel and/or inject chemicals into enclosure 504a and/or drum 513. In a further example, chemical reservoir 562 and/or nozzles 561 may be keep at a pressure between about 30 pounds per square inch and 40 pounds per square inch.

The chemical(s) disposed in chemical reservoir 562 may be configured to accomplish several things. For example, the chemical may be configured to destroy biological contaminants and/or neutralize chemical contaminants. In another example, the chemical may be configured to coat and/or penetrate the articles. In a further example, the chemicals may be configured to, once applied to the articles, increase the effectiveness of the heat treatment, microwave treatment, and ultraviolet light treatment in destroying biological contaminants and/or neutralizing chemical contaminants. The chemical may be non-toxic, for example, so as to be easily handled by the user, and even if a leakage occurs, is not harmful to the user. However, more toxic chemicals may also be used, for example, if the toxic chemicals are more effective in implementing one of the objectives of the chemicals set forth herein. The chemical may be a pesticide, and thus may need to be placed on the Environmental Protection Agency's chemical register.

In some embodiments, the chemical may be a water-based solution. For example, the chemical may comprise about 95% water and about 5% alcohol. However, other concentrations of water and alcohol may be used (e.g., the chemical may comprise anywhere between about 100% water to 0% water and/or about 0% alcohol to about 100% alcohol, possibly in 5% increments). The water-based solution may interact with the heat generated by heat treatment apparatus 530, the microwave energy emitted microwave apparatus 540, and the ultraviolet light emitted by ultraviolet light emitting apparatus 550, 551, 552 to more effectively destroy biological contaminants and/or neutralize chemical contaminants. For example, the water-based solution may allow heat and/or ultraviolet light to more effectively penetrate the articles. In another example, the water-based solution may be excited by the microwave energy and further increase the temperature in enclosure 504a and/or drum 513. The water-based solution may be introduced via nozzle(s) 561 into enclosure 504a and/or in cavity 514 after the temperature in enclosure 504a and/or in cavity 514 has reached a certain temperature, for example, about 130° C. The water based solution may be injected into enclosure 504a and/or cavity 514 at several times during a single operating cycle, for example, at a rate of about 15 milliliters every two minutes.

Figure 6:
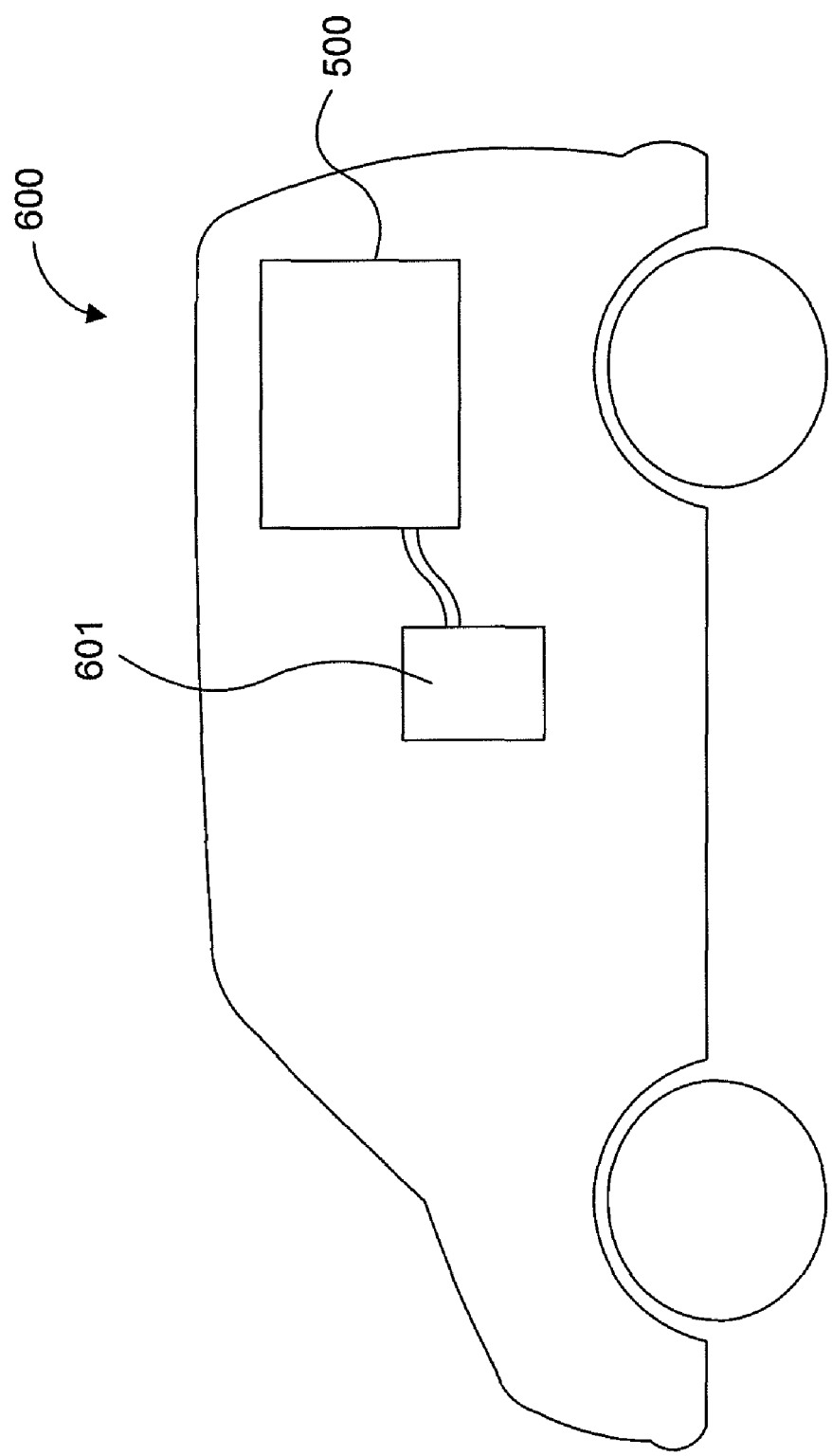
FIG. 6 is a schematic view of a vehicle that includes the articles processor of FIG. 5A.

Another embodiment of the invention includes a vehicle (e.g., automobile, aircraft, helicopter) including an articles processing system, for example, system 100 or system 500. For example, as shown in FIG. 6, system 500 may be placed in a sports utility vehicle 600 with a dedicated power source 601 configured to provide sufficient power to run system 500. Vehicle 600 is advantageous because it is a mobile system that may allow emergency response and/or third party personnel to respond to a articles emergency. For example, should an office building or other facility suspect that some articles they have received may be contaminated with biological/chemical contaminants, vehicle 600 could be brought to the specified location and the possibly contaminated articles could be decontaminated and/or neutralized by processing the articles using any of the systems (e.g., system 100, 500) or methods set forth herein.

Figure 7:
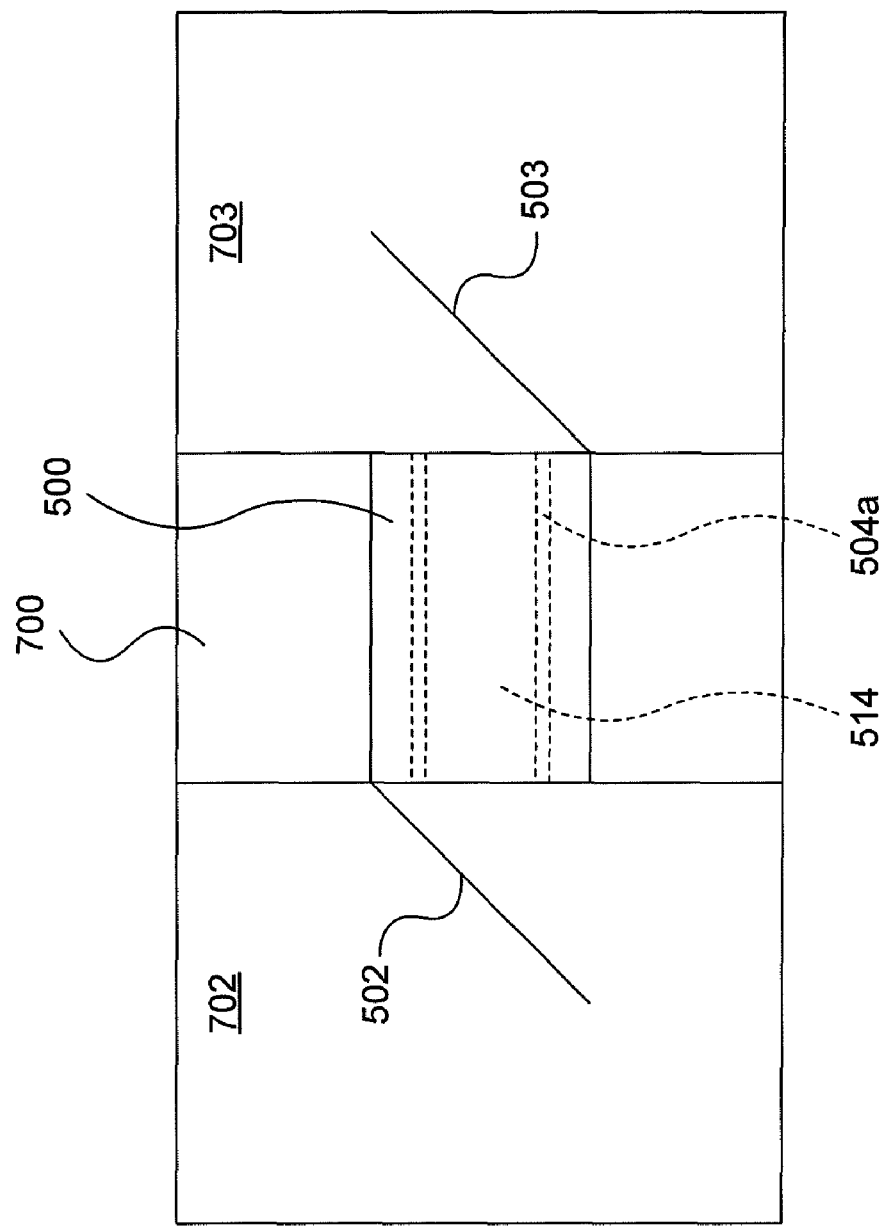
FIG. 7 is a schematic view of two rooms and a wall that include the articles processor of FIG. 5A.
Figure 8B:
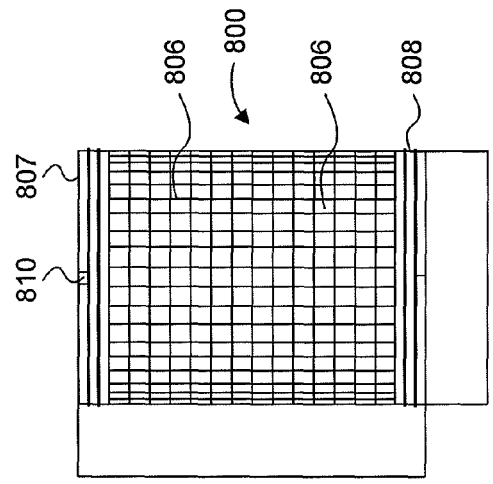
FIGS. 8A-8D are schematic views of a drum according to a further embodiment of the invention.
Figure 8D:
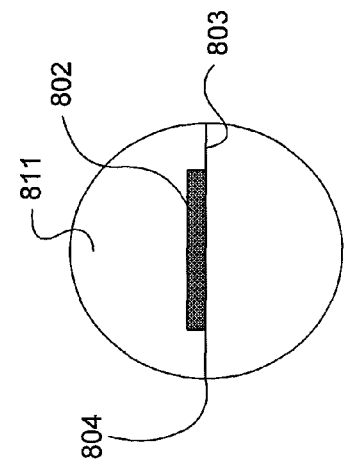
Figure 8A:
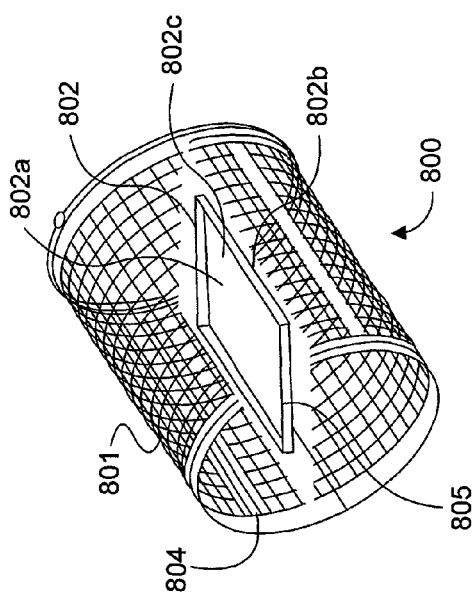
Figure 8C:
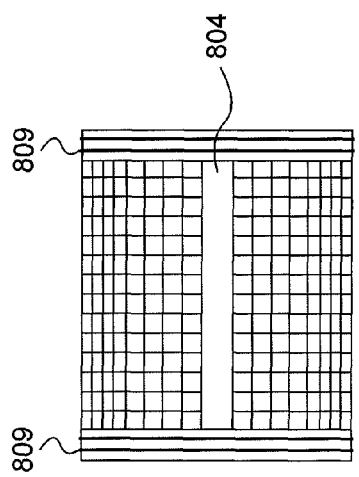

Yet another embodiment of the invention includes a system 100, 500 disposed in a wall between two rooms. For example, as shown in FIG. 7, system 500 may be disposed in a wall 700 between two rooms 701, 702. First door 502 may open into room 701 while second door 503 may open into room 702. First room 701 may be a "dirty" room where potentially contaminated articles may be sorted and then placed into enclosure 504a and/or cavity 514 via the opening covered by first door 502. Second room 702 may be a "clean" room where articles decontaminated by system 500 may be removed from enclosure 504a and/or cavity 514 via the opening covered by second door 503. Such a configuration may be advantageous, for example, to ensure that decontaminated articles in clean room 703 are not inadvertently contaminated with contaminants from potentially contaminated articles from dirty room 702.

Another embodiment of the invention may include a system 100, 500 for treating contaminated documents and papers. System 100, 500 may include a drum 800 configured to hold documents, examples of which are shown in FIGS. 8A-8D. Drum 800 may replace drum 110 in system 100 or drum 513 in system 500. Indeed, drum 800 may include any aspect of drum 110 or drum 513.

Drum 800 may include a cylindrical portion 801 defining a cavity 811. Cylindrical portion 801 may include a plurality of perforations 806. Perforations 806 may be configured to allow any combination of heat, air, chemical(s), microwave energy, ultraviolet light, and/or radiation therethrough. Cylindrical portion 801 may include a first end 807 and a second end 808. One or more of first end 807 and second end 808 may include one or more protrusions 809. Protrusions 809 may be configured to interact with any portion of systems 100, 500 configured to rotate drum 800, for example, wheels 516w. First end 807 may also include a protrusion 810.

Drum 800 may include a holder 802 configured to hold documents (e.g., saturated documents) during rotation of drum 800 and/or operation of system 100, 500. Holder 802 may include a tray portion 802b and a lid portion 802a defining a cavity 802c. Lid portion 802a may be movable relative to tray portion 802b, and may be connected to tray portion 802b using any suitable connector and/or method, for example, via latch 805. Latch 805 may be any suitable latch configured to hold lid portion 802a and tray portion 802b together during rotation of drum 800 and/or operation of system 100, 500 when documents are disposed in cavity 802c. Lid portion 802a and tray portion 802b may be configured to allow any combination of heat, air, chemical(s), microwave energy, ultraviolet light, and/or radiation therethrough. For example, lid portion 802a and tray portion 802b may include perforations and/or may be made out of any material configured to allow any combination of heat, air, chemical(s), microwave energy, ultraviolet light, and/or radiation therethrough.

Holder 802 may be attached to a portion 804 of cylindrical portion 801 via connector 803. Connector 803 may be fixedly or detachably be connected to holder 802 using any suitable method or device. Connector 803 may be connectable to and/or detachable from portion 804 using any suitable connection and/or method. Holder 802 and/or connector 803 may be disposed in a plane substantially parallel to and/or including a longitudinal axis of cylindrical portion 801, however, holder 802 and/or connector 803 may be disposed in any suitable configuration relative to cylindrical portion 801. Connector 803 may be configured to fix holder 802 relative to cylindrical portion 801, for example, so that holder 802 does not move relative to cylindrical portion 801 during rotation of drum 800 during operation of system 100, 500.

A further embodiment of the invention includes a method of using system 500, for example, during a decontamination/neutralization cycle. The method may include obtaining articles to be decontaminated or that may need to be decontaminated, such as mail, opening first door 502, and placing the articles in drum 513. While articles are placed in drum 513, second door 503 may be closed. First door 502 may then be closed and latched to housing 506. First door 502 may be closed such that gasket 507 is pressed against a surface of housing 506 so as to create a substantially fluid tight seal. First door 502 may be latched to housing 506, for example, via latch 510. Latch 510 may include two sets of latches: mechanical latch portions 510a, 510b and magnetic latch portions 510c, 510d. Mechanical latch 510 may latch when protrusion 510a is placed in aperture 510b and secured using any suitable mechanical latch structure and/or method. Magnetic latch 510 may latch when the poles of first magnetic portion 510c matches up with the opposing poles of second magnetic portion 510d. Once both latches 510 latch, sensor 511 may send a signal to processor 512 that first door 502 has been secured.

Substantially at the same time that sensor 511 detects that first door 502 is closed, sensor 511 may also confirm that second door 503 is closed. Second door 503 may includes latches similar to first door 502. Once sensor 511 sends signals to processor 512 that both first door 502 and second door 503 have been latched and/or secured, processor may allow power to flow to various portions of articles processor 501. For example, processor 512 may allow power to flow to and/or activate actuator 516a. In turn, actuator 516a may drive belts 516-1, 516-2, causing drum 513 to rotate. Drum 513 may rotate along with belts 516-1, 516-2, and may be held in place by wheels 516w. Drum 513 may rotate at a speed up to about 20 revolutions per minute, however, drum 513 may rotate at a speed up to about 30 revolution per minute.

Processor 512 may also activate and/or allow power to flow to heat treatment apparatus 530. Heat treatment apparatus 530 may include a heating element configured to raise and maintain the temperature inside enclosure 504a and/or cavity 514 at between about 250° F. and about 320° F. (and/or between about 120° C. and about 150° C.) at about 1000 Watts. Perforations 513p of drum 513 may allow heat to enter cavity 514 and the rotation of drum 513 may assist in circulating the heated air about cavity 514. Heat treatment apparatus 530 may raise and maintain the temperature inside enclosure 504a and/or cavity 514 at the desired temperature for the entire duration of the cycle, for example, up to about 30 minutes.

However, the entire cycle may also take up to about 45 minutes and/or heat treatment apparatus 530 may run for only a portion of the cycle. Processor 512 and/or heat treatment apparatus 530 may be configured to maintain the temperature inside enclosure 504a and/or cavity 514 within a margin of error of about 2 percent. One or more of housing 506, housing 506a, first door 502, and second door 503 may include a layer of insulating material, such as AMSS, configured to absorb heat and/or prevent heat from escaping enclosure 504a, for example, so that it does not harm a user or damage processor 512 disposed in enclosure 504 defined by housing 506. Another purpose of the layer of insulating material, such as AMSS, may be to allow the temperature in enclosure 504a and/or cavity 514 to be raised rapidly (e.g., by trapping heat in enclosure 504a and/or cavity 514).

Processor 512 may also activate and/or allow power to flow to microwave apparatus 540. Microwave apparatus 540 may be configured to provide microwave energy to enclosure 504a and/or cavity 514 at between about 500 Watts and about 1000 Watts at 2.4 GHz. Housing 506a, drum 513, and/or perforations 513p may be configured to allow microwave energy to pass therethrough. Surfaces of drum 513 and housing 506a defining cavity 514 and enclosure 504a, respectively, may be configured to reflect microwave energy within cavity 514 and enclosure 504a, for example, to prevent microwave energy from exiting articles processor 501 in sufficient quantities to harm users and/or to increase the effectiveness of the microwave treatment on the articles. Protrusions 502, 503a on doors 502, 503 may also be configured to have a highly reflective surface so as to prevent microwave energy from exiting articles processor 501 via doors 502, 503 in sufficient quantities to harm users and/or to increase the effectiveness of the microwave treatment on the articles. Microwave apparatus 540 may apply microwave energy to articles during the entire cycle (e.g., up to about 30 minutes) or only a portion of the cycle.

Processor 512 may also activate and/or allow power to flow to ultraviolet light emitting apparatus 550. For example, processor 512 may activate and/or allow power to flow to first ultraviolet light emitting apparatus 551 and second ultraviolet light emitting apparatus 552. Processor 512 may cause pulsed lights 553, 554 to emit a pulsed ultraviolet light at a wavelength of between about 190 nanometers and 2000 nanometers, a frequency of about 50 Hz, and/or at a power output of about 60 Watts. The timing of the pulses of ultraviolet light may be any suitable time interval and may vary in length. Pulsed lights 553, 554 may emit ultraviolet light at different portions of enclosure 504a and/or cavity 514, for example, by being disposed at different locations about housing 506a and/or enclosure 504a. Constant light 552 may be configured to emit ultraviolet light at a wavelength between about 249 nanometers and 254 nanometers and/or have a power output of about 150 microwatts per square centimeter. Ultraviolet light emitting apparatus 550 may apply ultraviolet light to articles during the entire cycle (e.g., up to about 30 minutes) or only a portion of the cycle.

Processor 512 may also activate and/or allow power to flow to chemical applicator 560. For example, the chemical may be a water-based solution having a composition of about 95% water and about 5% alcohol. The chemical may be disposed in chemical reservoir 562 having a capacity of about 1 gallon and/or at a pressure between about 30 pounds per square inch and 40 pounds per square inch. However, the chemical may be disposed in chemical reservoir 562 having any suitable capacity and at any suitable pressure. When activated, and after the temperature in enclosure 504a and/or cavity 514 reaches about 130° C., the chemical may flow from chemical reservoir 562 to nozzle(s) 561. Nozzle(s) 561 may then apply the chemical to enclosure 504a and/or cavity 514, for example, at a rate of about 15 milliliters at about two minute intervals in the cycle. During the cycle, about ½ cup (or about 4 fluid ounces) of the chemical may be used. When applied, the chemical may form a mist in enclosure 504a and/or cavity 514 where the droplets have a size on the order of about 10 microinches. The chemical may be applied to enclosure 504a and/or cavity 514 at approximately a seventy degree angle relative to a plane perpendicular to axis 515. Nozzle(s) 561 may be disposed about housing 506a, enclosure 504a, and/or cavity 514 in several places, for example, to allow for a more even distribution of the chemical into enclosure 504a and/or cavity 514. Once disposed in enclosure 504a and/or cavity 514, the chemical may assist in destroying biological contaminants and/or neutralizing chemical contaminants. For example, the chemical may come into contact with the articles and allow the heat and/or ultraviolet light to more easily and effectively penetrate the articles. In another example, the chemical may interact with the microwave energy to assist in destroying biological contaminants and/or neutralizing chemical contaminants.

Processor 512 may also activate and/or allow power to flow to fluid pump 579 so as to allow fluid (e.g., air, gas, and/or liquid) to flow into enclosure 504a from the outside environment, through fluid inlet 577 and any filters 581, through enclosure 504a and/or cavity 514, through fluid outlet 577 and any filters 582, 583, and then back to the outside environment.

Once the cycle has run for its allotted time period, processor 512 may deactivate and/or disconnect power from one or more of actuators 516a, heat treatment apparatus 530, microwave apparatus 540, ultraviolet light emitting apparatus 550, and/or chemical applicator 560. Once the temperature inside enclosure 504a reaches a safe level, second door 503 may be unlocked (e.g., by releasing the latches 510) and the articles may be removed from drum 513. The safe level of temperature as determined by the Occupation Safety and Health Administration may be about 70 degrees Celsius, however, the safe level of temperature may be higher if proper warnings and instructions are provided concerning the temperature level of the articles, the air in enclosure 504a, and/or the air in cavity 514. Second door 503 may then be closed (e.g., by reactivating the latches) and system 500 may be prepped for another cycle. Processor 512 and/or latches 510 are configured such that should power be cut from articles processor 501 in the middle of a cycle, latches 510 will not allow doors 502, 503 to open until power is restored and the processor 512 can determine (e.g., via sensors disposed in enclosure 504a and/or cavity 514) that the conditions are safe (e.g., the temperature is low enough, microwave apparatus 540 has been turned off, ultraviolet light emitting apparatus 550 has been turned off, and/or chemical applicator 560 no longer expels chemicals).

A further embodiment of the invention may include a method of treating contaminated articles, for example, documents that have become saturated and/or contaminated with chemicals, bacteria, fungi, viruses, and/or soil as a result of flooding. Exemplary articles include folders, documents, manuals, and carbon copies of documents. Saturated articles may weigh about 53 pages per pound, however, any document with any level of moisture and/or contaminants may be treated using any system or method set forth herein.

In such a method, up to about one pound of a fully saturated article may placed in a water-based solution that contains a mild disinfectant. The mild disinfectant may include chemicals similar to the chemicals in LISTERINE ANTISEPTIC solutions or any other chemicals that may be used with system 100, 500, for example, a water-based solution having a composition of about 95% water and about 5% alcohol. The fully saturated articles may then be placed in cavity 802c of holder 802 of drum 800. The amount of saturated articles placed in drum 800 may vary based on a variety of factors, for example, saturation level (e.g., greater than 20% moisture by weight), weight, and volume. Lid portion 802 and tray portion 802b may then be closed and secured via latch 805. Holder 802, which is connected to connector 803, may then be placed in cavity 811 of cylindrical portion 801. Ends of connector 803 may be secured to portion 803 of cylindrical portion 801 using any suitable method and/or devices.

Once secured, system 100, 500 including drum 800 may be operated and the fully saturated articles may be processed using any combination of steps set forth herein, at any suitable temperature (e.g., about 160° C.), for any suitable length of time, for example, about 50 minutes. Wheels 516w may be used to rotate drum 800 via protrusions 809. Once processed, the articles may be removed from system 100, 500. For example, connector 803 may be detached from portion 804. Holder 802 and/or connector 803 may then be removed from cavity 811. Latch 805 may be unlatched so as to allow lid portion 802 to move relative to tray portion 802b. The articles may then be removed from cavity 802c and copied, scanned, or otherwise duplicated using any suitable method or device, for example, scanned into a computer's memory system for future retrieval. Upon processing of the saturated and/or contaminated articles as set forth herein, the articles are suitable for human handling.

In one exemplary embodiment, system 100, 500 including drum 800 may be operated in the following manner. Upon placement of the saturated articles in cavity 811 and placement of drum 800 in system 100, 500, drum 800 may be spun up to its operational rotational speed in about 10 seconds. The saturated articles may also be heated for about 31 minutes at about 160° C. After about 31 minutes, the heater may be turned off and a chemical may be applied to drum 800, cavity 811, and cavity 802c via one or more of perforations 806, lid portion 802a, and tray portion 802b at a rate of about 15 milliliters at about three minute intervals in the cycle. Microwave energy and ultraviolet light may be substantially simultaneously applied to drum 800, cavity 811, and cavity 802c for two minute durations interspersed by one minute intervals. This may occur five times. During the four one minute intervals between the two minute durations, heat may be applied to drum 800, cavity 811, and cavity 802c. The chemical may be applied at substantially the same time that the application of microwave energy and ultraviolet light to drum 800, cavity 811, and cavity 802c is initiated. After about 14 minutes, the microwave energy and ultraviolet light may be turned off, and the heater may be turned on for about three minutes. After those three minutes, the heater may be turned off for one minute, the chemical may be applied to drum 800, cavity 811, and cavity 802c for a fraction of that one minute. After the one minute, the heater may be turned back on for an additional seven minutes, after which the heater may be turned off and a blower may be turned on for about eight minutes, for example, to apply dry air to and/or remove moist air from cavity 802c, 811. At the conclusion of the eight minutes, the operation may be concluded, the rotation of drum 800 may cease, and the formerly saturated products may be removed from system 100, 500. It should be understood that the aforementioned time values, amounts of chemicals, intensity of applied energy, and operational sequences are exemplary only, and that any suitable values may be used. Furthermore, the application of rotation, chemicals, microwave energy, heat, and ultraviolet light may be accomplished using any mechanism set forth herein or otherwise known in the art.

In various embodiments, a single decontamination cycle may run between about 45 minutes and about 60 minutes. During that time period, about 30 minutes of the single decontamination cycle may involve the heating of the air inside enclosure 504a and/or cavity 514 to the appropriate temperature. The balance of the time (e.g., between about 15 minutes and about 30 minutes) may be the other portions of the process, e.g., providing chemicals, providing microwave energy, and/or providing ultraviolet light.

In various embodiments, a single decontamination cycle may include steps executed in a particular order. For example, the cycle may begin by at least one of the doors (e.g., the "dirty" door or "contaminated" door) being opened. Thereafter, articles may be placed in the cavity, the doors may be closed, the doors may be locked, the closing and the locking of the doors may be verified, and then the powering up of the system may begin. Substantially simultaneously with the powering up of the system, an indicator light may indicate that the system is powered up, and the indicator light may continue to indicate that the system is powered up while power is being provided to the system. After a small delay following the locking of the doors (e.g., for about 10 seconds), the heat treatment apparatus may be turned on to begin heating up the air in the cavity. The air in the cavity may be continuously heated to a target temperature, for example, for about 30 minutes. Around the time that the air in the cavity reaches about the target temperature (e.g., within about 2% of the target temperature) and/or 30 about minutes has elapsed (e.g., give or take about 5 minutes), microwave energy, ultraviolet light, and/or the chemical may be provided to the cavity. Microwave energy, ultraviolet light, and/or the chemical may be continuously and/or intermittently provided to the cavity for about 10 minutes. For example, microwave energy may be continuously provided to the cavity for 10 minutes, a constant ultraviolet light may be provided to the cavity for about 10 minutes, pulsed (e.g., intermittent) ultraviolet light may be provided to the cavity for about 10 minutes, and/or the chemical may be intermittently applied to the cavity (e.g., in bursts of about 15 milliliters about every two minutes). After the microwave energy, ultraviolet light, and/or the chemical have been applied to the cavity for about 10 minutes, the microwave energy, ultraviolet light, and/or the chemical are deactivated. Substantially at the same time that the microwave energy, ultraviolet light, and/or the chemical are deactivated, the fluid exchange system removes the air, the chemical, and/or any decontaminants from the cavity. The fluid exchange system may run, for example, for about five minutes. Once the fluid exchange system has completed its job, various portions of the system may be powered down, at least one of the doors (e.g., the "clean" door or "decontaminated" door) may be unlocked, at least one of the doors may be opened, and the articles may be removed from the cavity.

The advantages of system 500 are numerous over previous systems for destroying biological contaminants and/or neutralizing chemical contaminants. For example, system 500 is relatively compact, and can easily placed and used in an office setting. In some embodiments, system 500 may have dimensions of about 28 inches by 32.7 inches by 30.6 inches, and may weigh about 285 lbs (or about 128 kilograms). In other embodiments, system 500 may have dimensions of about 30 inches by 20.9 inches by 31.38 inches. Due in part to its compactness, system 500 is portable, as it may be disposed on wheel or may easily be placed on a moving means. Also due in part to its compactness, system 500 may be stacked, for example, so as to maximize the use of vertical space while minimizing the use of floor space.

A further advantage is that system 500 is capable of destroying anthrax or other spores at a level that exceeds Occupational Safety and Health Administration (OSHA). For example, OSHA requires that the kill rate for anthrax or other spores be on the order of $10^6$. However, the kill rate for the system 500 and method described herein is on the order of at least $10^7$, and is effective on the order of $10^8$ and possibly even up to $10^9$.

System 500 consumes less than about 20 amps of 110/120V alternating current at about 50/60 Hz. Thus, it may simply be plugged into a standard United States wall socket. System 500 may consume about 15 amps at about 1920 Watts. It is contemplated that for use of system 500 with other types of outlets (e.g., 220V outlet used in at least parts of Europe and Asia), either a converter will be built into system 500, or one or more portions of system 500 will be exchanged for portions that require or are at least compatible with 220V outlets.

System 500 is easy to use, as once the system 500 has been plugged in, first door 502 is opened, articles is placed in drum 513, first door 502 is closed, and then the process is run. Once the process has been completed, second door 503 is opened, the articles is removed from drum 513, and the second door 503 is closed, completing the process.

Another advantage of system 500 is that it is not harmful to the user. For example, despite the use of microwaves, ultraviolet light, and/or heat, at least partially due to the insulation used in system 500, a user may stand next to system 500 without suffering harmful effects from any of the microwaves, ultraviolet light, and/or heat. Furthermore, because system 500 uses a water-based, non-toxic chemical, even if exposed to the chemical, the user is substantially, if not completely, unharmed. The system 500 may be configured to meet the regulatory requirements of OSHA, FDA, and EPA.

In various embodiments, system 100, 500 and the methods described herein may be used to decontaminate all kinds of articles. For example, system 100, 500 may be used decontaminate paper, currency, food, and/or medical supplies.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of decontaminating articles containing greater than 20% moisture by weight within an apparatus that includes a housing defining at least one opening, and an enclosure in flow communication with the at least one opening, at least one door configured to cover the at least one opening, respectively, and a rotatable drum in the enclosure, the rotatable drum defining a cavity, wherein the housing includes a layer of amorphous magnesium silicate fiber, the method comprising:

placing the articles in a water-based solution including a disinfectant;

placing the articles into the cavity via the at least one opening;

confirming that the at least one door is closed;

rotating the drum;

heating the air in the cavity;

providing microwave energy to the cavity;

providing ultraviolet light to the cavity from a plurality of ultraviolet light emitting apparatuses;

placing a chemical in the cavity;

opening the at least one door;

removing the articles from the cavity via the at least one opening; and creating an electronic copy of the articles.

2. The method of claim 1, further comprising placing the articles in a holder; and placing the holder in the drum.

3. The method of claim 2, further comprising connecting the holder to the drum such that the holder is fixedly disposed relative to the drum.

4. The method of claim 2, further comprising separating a first portion of the holder from a second portion of the holder;

placing the articles between the first portion and the second portion; and connecting the first portion and the second portion such that the first portion is fixedly disposed relative to the second portion.

5. The method of claim 2, further comprising placing up to about one pound of articles in the holder; and placing the holder in the drum.

6. The method of claim 1, further comprising placing the articles in the cavity for about 50 minutes.

7. The method of claim 1, further comprising heating the air in the cavity to about 160° C.

* * * * *